(12) United States Patent
Jain et al.

(10) Patent No.: US 11,043,139 B1
(45) Date of Patent: Jun. 22, 2021

(54) PROVIDING DIGITAL HEALTH INTERVENTIONS

(71) Applicant: VigNet Incorporated, Fairfax, VA (US)

(72) Inventors: Praduman Jain, Fairfax, VA (US); Josh Schilling, Newberg, OR (US)

(73) Assignee: Vignet Incorporated, Fairfax, VA (US)

( * ) Notice: Subject to any disclaimer, the term of this patent is extended or adjusted under 35 U.S.C. 154(b) by 9 days.

(21) Appl. No.: 16/433,419

(22) Filed: Jun. 6, 2019

Related U.S. Application Data

(63) Continuation of application No. 16/425,896, filed on May 29, 2019, now Pat. No. 10,565,894.

(51) Int. Cl.
*G09B 19/00* (2006.01)
*G16H 20/00* (2018.01)
*G06N 20/00* (2019.01)

(52) U.S. Cl.
CPC ............. *G09B 19/00* (2013.01); *G06N 20/00* (2019.01); *G16H 20/00* (2018.01)

(58) Field of Classification Search
CPC ......... G09B 19/00; G16H 20/00; G06N 20/00
See application file for complete search history.

(56) References Cited

U.S. PATENT DOCUMENTS

| | | | |
|---|---|---|---|
| 10,357,687 B1 | 7/2019 | Amos, III | |
| 10,565,894 B1 * | 2/2020 | Jain | G06N 20/00 |
| 2006/0025282 A1 * | 2/2006 | Redmann | A61B 5/1112 482/8 |
| 2008/0027673 A1 | 1/2008 | Trumm | |
| 2008/0146334 A1 | 6/2008 | Kil | |
| 2014/0067494 A1 * | 3/2014 | Squires | G09B 19/0038 705/14.1 |
| 2014/0257533 A1 | 9/2014 | Morris et al. | |
| 2014/0257535 A1 | 9/2014 | Morris et al. | |
| 2014/0372133 A1 | 12/2014 | Austrum et al. | |
| 2015/0134088 A1 | 5/2015 | Romeo et al. | |
| 2015/0142689 A1 * | 5/2015 | Squires | G01C 22/00 705/329 |
| 2017/0109499 A1 | 4/2017 | Doshi et al. | |
| 2017/0124288 A1 | 5/2017 | Gundlapalli | |
| 2018/0092536 A1 | 4/2018 | Sandler et al. | |
| 2018/0350173 A1 * | 12/2018 | Smith | G06F 21/604 |

(Continued)

*Primary Examiner* — Corbett B Coburn
(74) *Attorney, Agent, or Firm* — Fish & Richardson P.C.

(57) ABSTRACT

Systems and methods for personalized digital goal setting and intervention are provided. Embodiments of the system allow for effective management and implementation of interventions to change behaviors or health statuses of individuals or groups. Systems and methods may include setting a measurement goal relating to a behavior or a health status and generating a marker based on the measurement goal, receiving sensor data, determining that at least one of the measurement goal or the marker is satisfied, and executing a triggering action. The triggering action may include at least one of controlling access to a user device, controlling access to an application stored on a user device, controlling access of a user device to a network, controlling access of a user device to a website, displaying a notification on the user device, or transmitting a command to a remote device, including an instruction to control access to a physical space.

19 Claims, 13 Drawing Sheets

(56) References Cited

U.S. PATENT DOCUMENTS

| | | |
|---|---|---|
| 2019/0065993 A1 | 2/2019 | Srinivasan et al. |
| 2019/0068452 A1 | 2/2019 | Papadopoulos et al. |
| 2019/0079476 A1 | 3/2019 | Funes |

* cited by examiner

600

| | Behavioral Use Cases | | | | | |
|---|---|---|---|---|---|---|
| 602 Behavioral Interventions | Anxiety | Attention Deficit | Boredom | Depression | Disrupted Sleeping | Fatigue |
| | Loneliness | Loss of Appetite | Mental Health | Social Avoidance | Stress | Work/Life Balance |

| | Feature Classification | | | | | |
|---|---|---|---|---|---|---|
| 604 Applied Rules and Configurations | User is actively checking phone | User Biomarkers are changing | Phone intensely being utilized | User is watching Television | User is Sleeping | User is Eating |
| | User is actively using an app | Environment has a sudden change | User is showing interest | User Hasn't Moved | User is commuting | User is engaged in conversation |
| | User is rapidly changing apps | User is pacing | User is avoiding | Typing accuracy decreased | User is sleeping well | User is actively moving |
| | Fidget Spinning | Battery is rapidly depleting | Social proximity is increasing | User is shaking | Sleeping may be interrupted | Weather may be mood altering |

| | Sensor Types | | | | | |
|---|---|---|---|---|---|---|
| 606 Recipient Measurement Data | Audio / Video | Networking | Phone | Environment | Positioning & Activity | User Storage & Interactions |
| | Sensors | | | | | |
| | Raw Audio | Bluetooth State | App Class | Barometer | Accelerometer | Keyboard |
| | Audio Noise Classifiers | Bluetooth Nearby devices | App Name | Camera Image Detection | Altimeter | Screen |
| | Audio Transcripts | Network State | App Usage | Camera Light Wavelength | GPS | Touch |
| | Ambient Sound Level | Telephony State | App State | Ambient Light Levels | Gravity | Touch Patterns |
| | Microphone State | Wi-Fi State | Battery Level | Proximity | Gyroscope | User Health Storage |
| | Speaker Levels | Wi-Fi Nearby AP | Battery State | Temperature | Linear Accelerometer | Time Zone |
| | Speaker Control Adjustments | Call Log | SMS Content | Processor Usage | Location Classification | Magnetometer |
| | Audio Filtering | Phone Usage | SMS Log | Semantic Time | User Acceleration | Rotation |

FIG. 6

PROVIDING DIGITAL HEALTH INTERVENTIONS

This application is a continuation of application Ser. No. 16/425,896, filed May 29, 2019, the content of which is expressly incorporated herein by reference in its entirety.

BACKGROUND

People may desire to change behavior for improved health, happiness, well-being, performance, or other goals. Often, a person may have a goal that involves many aspects of that person's life and may be difficult to track or to change. For example, a person may desire to improve sleep quality, exercise more, adhere to a prescribed medication, improve diet, decrease cumulative screen time on various devices, spend more time with family or friends, spend more time doing homework, be more focused while working, have longer attention spans, or achieve other behavior outcomes. However, in today's complex technological environment with multiple distractions and opportunities for circumventing behavior restrictions, it may be difficult to track or change behavior.

In some cases, people may have goals related to behavior as part of a group. Any group of people may set a collective goal and wish to track progress towards that goal. For example, a family may have a group healthiness goal for spending more time together, reducing family screen time, exercising more, or the like. A team may have a group exercise goal for total number of hours spent exercising or total number of miles ran by team members in a time period. A class may have a group reading goal for hours spent studying, number of books read, or the like.

Conventional approaches for monitoring goals may include tools for sousveillance (lifelogging) or domotics (domus informatics or home automation), which may use data from various sources. For example, conventional approaches may collect data from Internet of Things (loT) devices. Some conventional systems may perform a simple action when an event occurs, such as preventing access to a website.

However, conventional approaches for tracking and changing individual or group behavior suffer from deficiencies. Often, conventional approaches provide simplified solutions that cannot address personalized medicine or personalized health issues, which may be complex. This may be because they involve triggers that are too simple to manage complex scenarios. Conventional systems and methods may not be capable of implementing fuzzy logic to track or modify behavior. Conventional approaches may fail to capture values of an individual based on context. Conventional systems may lack feedback loops for error correction or control factors to help the system automatically adapt. Instead, conventional systems may need to be repeatedly reprogrammed by humans. Conventional approaches may not include dynamic interventions to restrict, reward, or punish behavior.

The disclosure presented herein addresses these and other problems of current systems and methods. In light of the shortcomings of conventional approaches, there is a need for new systems and methods for setting a goal, monitoring a goal, and performing an intervention or modifying a behavior or a health status related to a goal.

BRIEF DESCRIPTION OF THE DRAWINGS

FIG. 6 is a diagram of an exemplary data structure for managing a measurement goal and performing an intervention, consistent with disclosed embodiments.

DESCRIPTION

Figure 1:
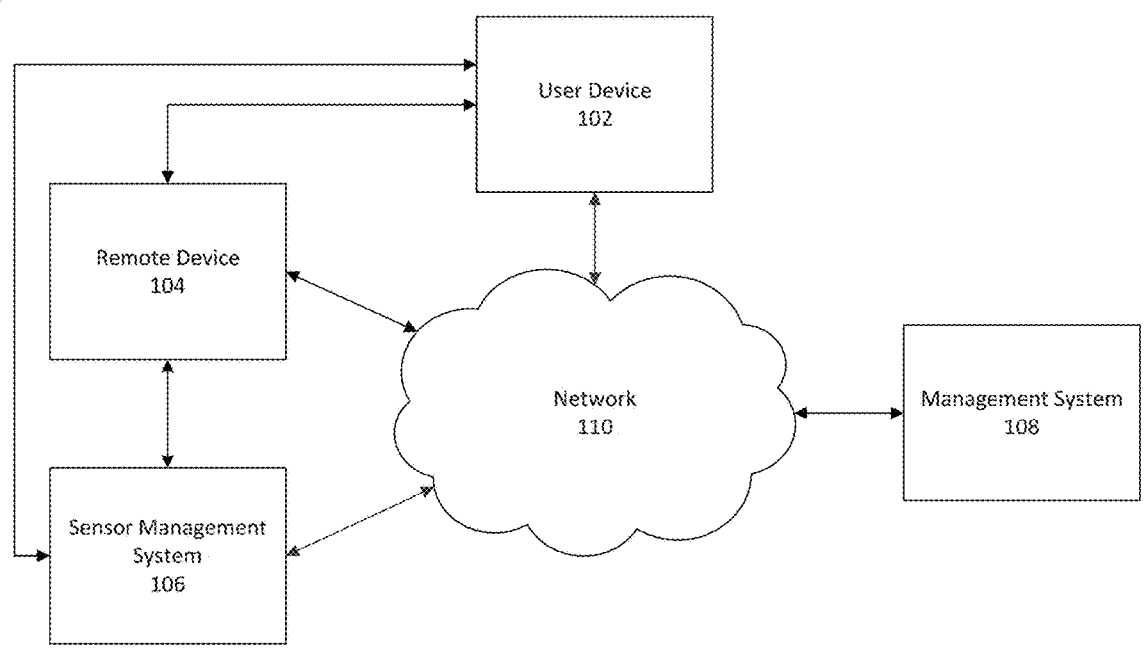
FIG. 1 is a diagram of an exemplary system for managing a measurement goal and performing an intervention, consistent with disclosed embodiments.

The disclosure provides tools for collecting and analyzing large amounts of data from a variety of sources, as well as tools for managing and implementing interventions to modify a behavior or a health status. In some embodiments, the disclosed systems provide a network of computers, comprised of a user device and associated data for managing an intervention. Embodiments include systems and methods for receiving data, carrying out processes, and/or generating outputs.

Consistent with the present embodiments, a system for managing and implementing an intervention is disclosed. The system may include one or more memory units storing instructions and one or more processors configured to execute the instructions to perform operations. The operations may include setting a measurement goal relating to at least one of a behavior or a health status and/or generating a marker based on a measurement goal. The operations may include receiving sensor data. The operations may include determining, based on sensor data, that at least one of a measurement goal or a marker is satisfied and/or executing a triggering action based on at least one of a measurement goal or a marker. A triggering action may include at least one of controlling access to a user device, controlling access to an application stored on a user device, controlling access of a user device to a network, controlling access of a user device to a website, displaying a notification on a user device, and/or transmitting a command to a remote device that includes an instruction to control access to a physical space. The operations may include receiving additional sensor data and/or adjusting a measurement goal and/or a marker based on the additional sensor data.

Consistent with the present embodiments, a method for managing and implementing an intervention is disclosed. The method may include setting a measurement goal relating to at least one of a behavior or a health status and/or generating a marker based on the measurement goal. The method may include receiving sensor data. The method may include determining, based on sensor data, that at least one of a measurement goal or a marker is satisfied and/or executing a triggering action based on at least one of a measurement goal or a marker. A triggering action may comprise at least one of controlling access to a user device, controlling access to an application stored on a user device, controlling access of a user device to a network, controlling access of a user device to a website, displaying a notification on a user device, and/or transmitting a command to a remote device that includes an instruction to control access to a physical space. The method may include receiving additional sensor data and/or adjusting a measurement goal and/or a marker based on the additional sensor data.

Consistent with other disclosed embodiments, non-transitory computer readable storage media may store program instructions, which are executed by at least one processor device and perform any of the methods described herein.

Embodiments may include digital phenotyping. Digital phenotyping may include a classification and/or a quantification of a behavior or a health status of an individual based on evidence-based measurable marker as it may relate to physiological signals, observed through measurable changes and/or collected through biosamples, genomics and/or omics discoveries, personalized characteristics (attributes specific to an individual), lifestyle and/or behavior data collected by digital devices, including sensor data (e.g., such as sleep monitoring, activity monitoring) and/or app usage. Digital phenotyping may relate to prognostics or diagnostics of health history, health behaviors, health status, disease conditions, including physical, social, or mental diseases, behavioral health.

Embodiments consistent with the present disclosure may include a group of individuals. Groups may include any type of group of people, such as a family, a team, employees, co-workers, members of an organization, a group of friends, a class, parents, a community group, a neighborhood group, a group of groups, a society, or the like. Groups may be of any size. A group may include individuals related based on genealogy, likes/dislikes, subscription relevance, education, residence location, individuals linked by a study or a substudy within a cohort, and/or any other relationship.

Embodiments consistent with the present disclosure may include a system and/or method for personalized digital goal setting and intervention. A personalized digital goal may include an individual measurement goal and/or a group measurement goal, consistent with disclosed embodiments. A personalized intervention may include an intervention to change a behavior or a health status of an individual or a group as a whole, consistent with disclosed embodiments.

Embodiments consistent with the present disclosure may include a measurement type related to a behavior and/or a health status. A measurement type related to a behavior may include an internet usage, a screen time, a video game usage, a social media usage, an exercise pattern, a diet, a sleep pattern, a medication adherence, or any other behavior. A measurement type associated with a health status may include a body mass index, a heart rate measure, a breathing measure, a blood pressure measure, a hydration measure, a sleep quality score, an anxiety score, a depression score, or any other health indicator.

Embodiments consistent with the present disclosure may include a measurement goal. A measurement goal may be based on a measurement type. In some embodiments, a measurement goal may relate to a behavior or a health status. A measurement goal may include an internet use goal, a diet goal, a consumption goal, a sleep goal, an exercise goal, a medical treatment goal, or an activity goal. A measurement goal may include a threshold (i.e., a minimum or a maximum) of an indicator of a behavior or a health status. Examples of measurement goals may include a minimum number of hours spent studying during a week, a maximum anxiety score, a resting heart rate threshold, a maximum screen time, a minimum number of social interactions, a vegetables-consumed threshold, a medication adherence minimum, and/or any other threshold of an indicator of a behavior or a health status. In some embodiments, a measurement goal may include a coding function for processing data (e.g., sensor data). A coding function may include check statements, when statements, while statements, do statements, Boolean logical statements, or the like. In some embodiments, setting a measurement goal may include a machine learning model trained to predict an indicator of a behavior or a health status. In some embodiments, a measurement goal may include a fuzzy logic model, which may or may not be a machine learning model.

Embodiments consistent with the present disclosure may include a marker. A marker may include a condition that may predict whether a measurement goal is likely to be satisfied in the future. For example, a maker may include an estimate of whether a student is likely to satisfy a measurement goal of studying for at least ten hours between a Monday and a Sunday based on a present cumulative number of hours spent studying (e.g., a number of hours spent studying as of Wednesday). As another example, a marker may be based on a coding function or model that accepts alcohol consumption data, motion data, and screen time data, as input and estimates whether a user is likely to meet a sleep quality measurement goal.

Embodiments consistent with the present disclosure may include interventions to change a behavior or a health status of an individual. An individual may be a member of a group (e.g., a family, a team, employees, co-workers, members of an organization, members of a community, a group of friends, a class). Interventions may be managed by the individual himself or herself. Interventions may be managed by an administrator (e.g., a group leader, a coach, an employer, a parent).

Embodiments consistent with the present disclosure may include interventions to change a behavior or a health status of a group as a whole. For example, an intervention may relate to a group measurement goal comprising a limit on the total amount of time two or more family members spend doing a particular activity without setting a measurement goal for individual family members doing that activity. As another example, an intervention may relate to a group measurement goal comprising a total number of miles walked by all members of a social club.

Embodiments may include interventions to change a behavior or a health status of individuals within a group and to change a behavior or a health status of a group as a whole. For example, for a group of four individuals, an intervention may relate to a group measurement goal of 28 hours of exercise per week with respective individual measurement goals of 5 hours of exercise per week for each individual in the group. As another example, an intervention may relate to a group measurement goal of a percentage of compliance with individual measurement goals.

Embodiments consistent with the present disclosure may include triggering actions. Triggering actions may include controlling access to a computing resource (e.g., a device, an app, a network, a website). Triggering actions may include controlling access to a physical space (e.g., opening, closing, locking, and/or unlocking a door, a cabinet, a freezer, a pantry, a break room). Triggering actions may include transmitting or displaying a notification. Triggering actions may include a reward or a punishment. A reward or a punishment may include changing a measurement goal (e.g., increasing or decreasing a threshold related to a behavior such as increasing a screen time limit or changing the hours that a pantry may be unlocked).

In an illustrative example of an embodiment consistent with the present disclosure, a family may provide instructions to a management system to set a first measurement goal of 20-hours of combined internet use per week. The family may also set a second measurement goal related to an indicator of the quality of family-interaction time.

In this exemplary embodiment, family-member A may be struggling with homework and spending a large amount of time on a user device online to conduct research. A system may receive data from the user device and send a notification to another user device associated with family-member B. The notification may include a marker indicating that family-member A has exceeded a threshold (e.g., the marker may be 50% of the internet use group measurement goal or 10-hours of internet use). Family-member B may then approach family-member A, discover the problem with homework, and help family-member A to resolve the problem by discussing study strategies or by tutoring family-member A.

In this example, the discussion or tutoring may include high-value family-interacting time. Either family-member A or family-member B may self-report this family interaction to the management system. Alternatively or additionally, the management system may identify the family interaction from sensor data (e.g., from microphone data, location sensor data, or sensor data indicating stress levels of family-member A). The management system may estimate the quality of time using algorithms (e.g., machine learning models). As a result, the management system may determine that the family has satisfied the second measurement goal related to the indicator of the quality of time a family spends interacting. Or, the management system may determine that the family has satisfied a marker indicating progress towards the second measurement goal. Accordingly, the management system may execute a triggering action by sending a reward to the family and/or to family-member B (e.g., increase family-member B's allowed internet time).

The disclosed systems and methods may be implemented using a combination of conventional hardware and software as well as specialized hardware and software, such as a machine constructed and/or programmed specifically for performing functions associated with the disclosed method steps. The foregoing and following descriptions are exemplary and explanatory only and are not restrictive of the claims.

FIG. 1 is a diagram of an exemplary system 100 for managing a measurement goal and performing an intervention, consistent with disclosed embodiments. System 100 may include one or more components. System 100 may include, for example, a user device 102, a remote device 104, a sensor management system 106, and/or a management system 108. System 100 may include one or more of each component, it may include only some of these components, and it may include other components not depicted in FIG. 1.

Components of system 100 may be arranged in various ways. Components of system 100 may, for example, be connected to each other through a network, e.g., network 110. Components of system 100 may be directly connected via physical connections (e.g., a cable connection) or wireless connections (e.g., a BLUETOOTH connection). System 100 may include one or more of each connection, it may include only one of these connections, and it may include other connections not depicted in FIG. 1.

User device 102 may include a smartphone, a computer, a wearable device, a tablet, a mobile device, a terminal, a kiosk, a client device, and/or any other computerized device, consistent with disclosed embodiments. User device 102 may include a personal management device, consistent with disclosed embodiments. User device 102 may include hardware, software, and/or firmware. User device 102 may include one or more memory units for storing instructions and one or more processors for executing the instructions to perform operations.

User device 102 may include an interface, such as a user interface, comprising an input device and/or an output device. An input device and/or an output device of user device 102 may include a display, a touch screen, a light emitting component, a microphone, a speaker, a sensor, a haptic feedback device, a keyboard, a mouse, a track pad, or any other input device or output device.

User device 102 may be configured to receive and transmit data to and from components of system 100 or computing components outside system 100. For example, user device 102 may be configured to receive and transmit data relating to managing a measurement goal or performing an intervention, consistent with disclosed embodiments. User device 102 may be configured to collect data relating to one or more users. User device 102 may include received or collected data relating to one or more users.

User device 102 may be configured to support one or more users. For example, user device 102 may store and manage data associated with one or more users for managing measurement goals and interventions, consistent with disclosed embodiments.

User device 102 may include data related to an intervention. An intervention may thus be assigned or selected based on user input. An intervention may include performing actions for positive reinforcement of a behavior. An intervention may include performing actions for negative reinforcement of a behavior. An intervention may thus be assigned or selected based on data received from management system 108. An intervention may include data accessible by one or more users according to respective permissions level. For example, an administrator permission level may allow access to data associated with a plurality of users within a group, while an individual user permission level may limit access to a data associated with a subset of users within a group (e.g., to limit access to a data associated with a single user).

User device 102 may include data related to a measurement goal and the management of a measurement goal. User device 102 may be configured to create a measurement goal. Creating a measurement goal may be based on user input.

User device 102 may include data relating to rules and conditions of the user device and/or of one or more remote device. User device 102 may be configured to manage data sources and data collection. For example, user device 102 may be configured to send an instruction to a remote device. The instruction may be to change a setting. The instruction may be to transmit sensor data. The instruction may be to grant or deny access to a physical space.

User device 102 may include algorithms to analyze user data, including sensor data. In some embodiments, user device 102 is configured for performing fuzzy logic. Fuzzy logic may include classifications that describe a general truth. For example, a general truth may be classified as "mostly", "close to" a value, or "nearing" a value.

User device 102 may include algorithms to identify and correct errors in assessing progress towards a measurement goal. For example, user device 102 may include machine learning models for error correction.

User device 102 may be configured to generate a marker and/or determine whether a marker is satisfied. A marker may include a logical expression. The condition may be based on sensor data. For example, the condition may be whether a user is at home, at school, or at work. The logical expression may be a complex expression based on a plurality of sensor data. A marker may include fuzzy logic.

Further details of user device 102 are provided below in reference to FIG. 2.

Remote device 104 may include any computerized device. Remote device 104 may include hardware, software, and/or firmware. Remote device 104 may include one or more memory units for storing instructions and one or more processors for executing the instructions to perform operations. Remote device 104 may include a mobile device, a fitness-tracking device, a computer, a tablet device, a kiosk, a hub, a set top box, a digital assistant, an internet television device, a personal wearable device, an internet-of-things (IoT), or a device configured to perform operations.

Remote device 104 may include a sensor for collecting data. For example, remote device 104 may include an embedded sensor, an environmental sensor, a sensor attached to a person, a sensor embedded in a person, a sensor at a fixed location, a sensor on a moving object (e.g., a sensor located in or on a vehicle), a dedicated sensor (i.e., a sensor used primarily to collect data for a dedicated purpose), and/or any other sensor. In some embodiments, remote device 104 is a sensor.

Remote device 104 may include an active sensor. A remote device with an active sensor may be configured to receive instructions and collect data based on the instructions. A remote device with an active sensor may require particular user activities during data collection. For example, to produce accurate measurements, a remote device that includes a blood pressure sensor may require a user to sit, place a cuff on an upper arm, and initiate data collection by providing an instruction (e.g., pressing a touch screen).

Remote device 104 may include a passive sensor. A passive sensor may be configured to collect data without receiving instructions and/or follow an initial set of instructions without requiring particular user activities during data collection. For example, a sensor may be configured to monitor use of a device, including position or usage related to screen time, application time, call time, messaging, or the like. A passive sensor may be configured to collect data when a condition is met. For example, a passive sensor may be configured to collect data when it is held by a user or otherwise carried by a user. Non-limiting examples of a remote device with a passive sensor may include a device for measuring air quality in the home, a watch that collects heart rate, or a patch that measures galvanic skin response.

A sensor of remote device 104 may include, for example, a location or positioning sensor (e.g., a GPS sensor), a relative location or positioning sensor (e.g., a received signal strength indicator from a wireless access point, cellular tower, a portable nearby sensor), a magnetic field sensor (e.g., a magnetometer), a light sensor (e.g., an ambient light sensor), an audio sensor (e.g., an ambient noise sensor), an orientation sensor (e.g., a gyroscope), a movement or motion sensor (e.g., an accelerometer, a light-based motion detector), a personal identification sensor (e.g., a fingerprint detector, an iris scanner, a face detection scanner), a moisture sensor (e.g., a humidity sensor), temperature sensor (e.g., a body temperature sensor, a skin temperature sensor, a room temperature sensor), an electrocardiography sensor (e.g., an ECG, an R-R interval detector, a heart rate monitor), an electroencephalography sensor (e.g., an EEG), a photoplethysmography sensor (e.g., a pulse rate monitor, a pulse oximeter), an electrodermal sensor (e.g., a galvanometer), an auscultation sensor (e.g., a stethoscope, a blood pressure monitor), a blood-chemistry sensor (e.g., a glucose monitoring sensor, a ketone monitoring sensor), a load sensor (e.g., a weight scale sensor), a barometric pressure sensor (e.g., a barometer, an altimeter), a wave-detection sensor (e.g., a lidar sensor, a radar sensor, a sonar sensor), a gas sensor (e.g., a chromatography sensor, a smoke detector, an alcohol sensor, a dust particle sensor), and/or a water sensor (e.g., a chemical sensor, a turbidity sensor, a flow meter).

Remote device 104 may include an access device configured to control access to a physical space. An access device may include a device configured to authorize access. For example, an access device may include a door key fob scanner, a fingerprint scanner, a touchpad, or the like. An access device may include a mechanism for locking, unlocking, opening, and/or closing a barrier to a physical space. For example, remote device 104 may include a door lock or an opening and closing mechanism for a door. As non-limiting examples, remote device 104 may include an access device configured to control access to a liquor cabinet, a freezer, a tap, an entertainment room, a garage, an exercise room, a spa, or any other physical space.

In some embodiments, remote device 104 may include data relating to a scenario. A scenario may include a sensor configuration (i.e., data indicating sensor settings). A scenario may describe how and when a sensor may be used.

In some embodiments, remote device 104 may include data relating to a trigger. A trigger may include a sensor measurement, a pattern of sensor data, a time, a user input, an instruction, or a command.

In some embodiments, remote device 104 may be configured to perform an event based on a trigger, consistent with disclosed embodiments. An event may include turning a sensor on or off. An event may include data processing of sensor data. An event may include calibrating a sensor. An event may include controlling access to a physical space via an access device. An event may include enabling a remote device, disabling a remote device, changing a rate of data collection of a sensor, transmitting data, displaying data, or any other action performed by remote device 104.

Remote device 104 may include an interface, such as a user interface. An interface may include an input device and/or an output device. An interface may include a display, a touch screen, a light emitting component, a microphone, a speaker, a sensor, a haptic feedback device, a keyboard, a mouse, a track pad, and/or any other input device or output device.

Remote device 104 may be configured to receive and transmit data to and from components of system 100 or computing components outside system 100. For example, remote device 104 may be configured to receive and transmit data relating to managing a measurement goal or performing an intervention, consistent with disclosed embodiments. Remote device 104 may be configured to detect and/or automatically connect to another device, such as user device 102, another remote device, a sensor management system 106, and/or management system 108.

Remote device 104 may connect to network 110. Remote device 104 may directly connect to one or more other components of system 100. Remote device 104 may connect to network 110 or one or more other components of system 100 by a wireless connection and/or a wired connection. Additionally or alternatively, remote device 104 may be configured to connect to any other network. In some embodiments, a wireless connection may include a WI-FI communication connection, a BLUETOOTH communication connection, a LI-FI communication connection, a NEAR FIELD COMMUNICATION (NFC) connection, and/or an optical wireless communication connection. In some embodiments, a wired connection may include a UNIVERSAL SERIAL BUS (USB) connection, a FIREWIRE connection, an ethernet connection, and/or a cable connection.

Sensor management system 106 may include hardware, software, and/or firmware. Sensor management system 106 may include one or more memory units for storing instructions and one or more processors for executing the instructions to perform operations. In some embodiments, sensor management system 106 may include a personal computer, a server, a server cluster, and/or a cloud service. Sensor management system 106 may include data storage. Sensor management system 106 may include a Configuration Server (CFG) and/or an Access Control Server (ACS).

Sensor management system 106 may include data indicating availability (i.e., status) of a remote device such as remote device 104. For example, sensor management system 106 may include data indicating whether a remote device is connected to a network, whether a remote device produced an error message, whether a remote device is collecting data, whether a remote device needs maintenance, or the like.

Sensor management system 106 may include data relating to a scene. A scene may include a configuration of one or more sensors or one or more remote devices. For example, a configuration may include settings for coordinated data collection by a plurality of sensors.

Sensor management system 106 may include data relating to automation of a remote device. Automation may include data relating to a sensor setting. Automation may include data relating to a trigger. A trigger may include a sensor measurement, a pattern of sensor data, a time, a user input, an instruction, or a command.

Sensor management system 106 may include sensor data received from one or more remote devices.

Sensor management system 106 may be configured to send one or more instructions or commands to remote device 104. An instruction may relate to a trigger and/or automation. An instruction may be to change a setting of a remote device, such as a sensor setting that controls data collection. An instruction may be to start or stop data collection from a sensor. An instruction may be to transmit data to sensor management system 106 or another component of system 100.

Sensor management system 106 may include data relating to user device 102 (e.g., a personal management device). For example, sensor management system 106 may include data indicating whether a user device may access remote device data. Sensor management system 106 may include data relating to a user permission or user control.

Management system 108 may include hardware, software, and/or firmware. Management system 108 may include one or more memory units for storing instructions and one or more processors for executing the instructions to perform operations. In some embodiments, management system 108 may include a personal computer, a server, a server cluster, and/or a cloud service. Management system 108 may include data storage. Management system 108 may be configured for application management, user account management, group management, and/or individual management of measurement goals and/or interventions. Management system 108 may be configured to manage data collection across a plurality of user devices, remote devices, and sensor management systems. Management system 108 may be configured to manage an intervention across a plurality of user devices, remote devices, and sensor management systems. Further details of management system 108 are provided below in reference to FIG. 3.

One or more components of system 100 may connect to network 110. Data may flow between components in any direction in network 110. In some embodiments, network 110 may be a public network or a private network and may include, for example, a wired network or a wireless network. In some embodiments, network 110 may be a local area network (LAN), a wide area network (WAN), a metropolitan area network (MAN), an IEEE 802.11 wireless network, a WI-FI network, a network of networks, the Internet, and/or a land-line telephone network. In some embodiments, network 110 may be a secure network, for example, requiring a password or authentication for access.

Figure 2:
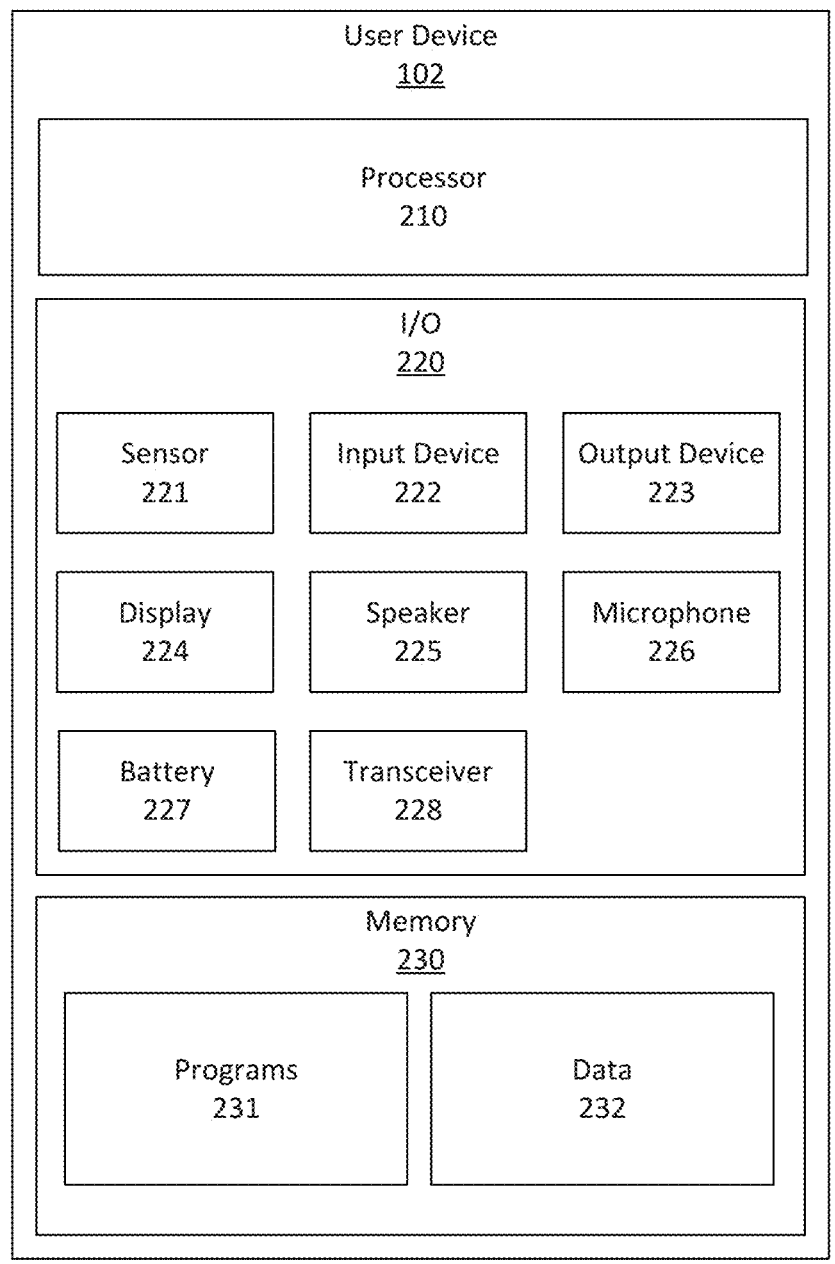
FIG. 2 is a diagram of an exemplary user device, consistent with disclosed embodiments.

FIG. 2 is a diagram of an exemplary user device 102, consistent with disclosed embodiments. User device 102 may include a smartphone, a computer, a wearable device, a tablet, a mobile device, a terminal, a kiosk, a client device, and/or any other computerized device, consistent with disclosed embodiments. User device 102 may include a personal management device, consistent with disclosed embodiments.

User device 102 may include one or more components. User device 102 may include, for example, a processor 210, an input/output (I/O) unit 220, and a memory 230. User device 102 may include one or more of each component, it may include only some of these components, and it may include other components not depicted in FIG. 2. Components of user device 102 may be arranged in various ways.

Processor 210 may be, for example, a computing processor. In some embodiments, processor 210 is a microprocessor. Processor 210 may be, for example, a single-core processor or a multiple-core processor (e.g., dual core, quad core). In some embodiments, processor 210 includes a single-core processor configured with virtual processing technologies. In some embodiments, processor 210 may include logical processors to simultaneously execute and control multiple processes. Processor 210 may implement technologies such as virtual-machine technologies to execute, control, run, manipulate, and/or store multiple processes, applications, and/or programs. In some embodiments, processor 210 may include a multiple-core processor configured to provide parallel processing functionalities for execution of multiple processes simultaneously. Processor 210 may be configured, for example, to execute one or more instructions stored in memory 230 to perform operations.

Figure 9:
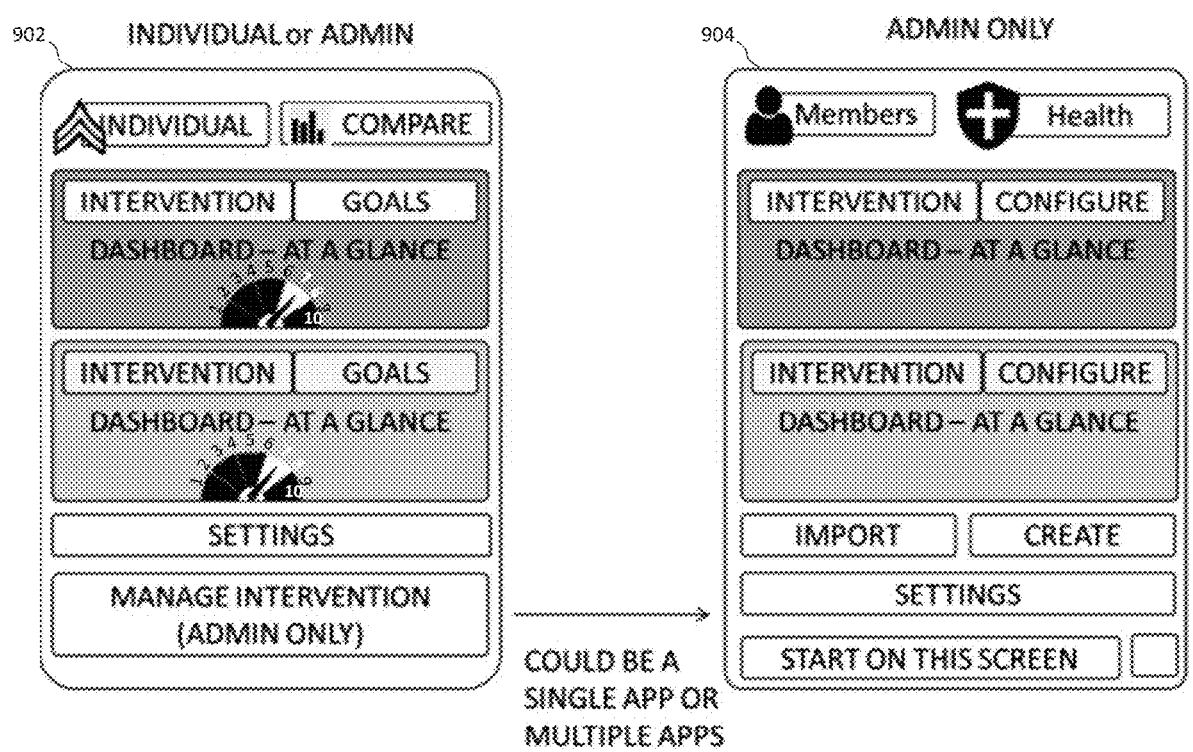
FIG. 9 is a diagram of exemplary user interfaces displaying user views, consistent with disclosed embodiments.
Figure 10:
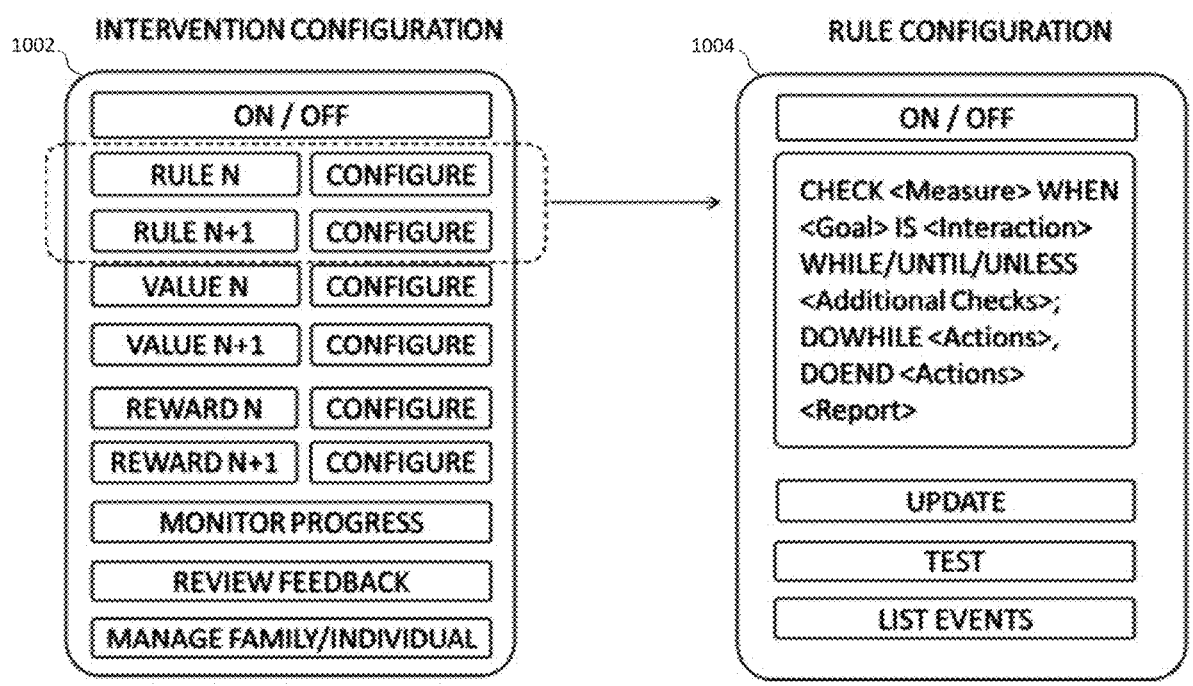
FIG. 10 is a diagram of exemplary user interfaces displaying administrator views, consistent with disclosed embodiments.

I/O unit 220 may include, for example, sensor 221, input user device 222, output user device 223, display 224, speaker 225, microphone 226, battery 227, and/or transceiver 228. In some embodiments, I/O unit 220 may be part of user device 102. In some embodiments, I/O unit 220 may be part of a different device that may be connected to user device 102. In some embodiments, I/O 220 may include components for receiving inputs and/or generating and displaying an interface as depicted in FIGS. 9, 10, and/or 11.

Sensor 221 may include, for example, a location or positioning sensor (e.g., a GPS sensor), a relative location or positioning sensor (e.g., a received signal strength indicator from a wireless access point, cellular tower, a portable nearby sensor), a magnetic field sensor (e.g., a magnetometer), a light sensor (e.g., an ambient light sensor), an audio sensor (e.g., an ambient noise sensor), an orientation sensor (e.g., a gyroscope), a movement or motion sensor (e.g., an accelerometer, a light-based motion detector), a personal identification sensor (e.g., a fingerprint detector, an iris scanner, a face detection scanner), a moisture sensor (e.g., a humidity sensor), temperature sensor (e.g., a body temperature sensor, a skin temperature sensor, a room temperature sensor), an electrocardiography sensor (e.g., an ECG, an R-R interval detector, a heart rate monitor), an electroencephalography sensor (e.g., an EEG), a photoplethysmography sensor (e.g., a pulse rate monitor, a pulse oximeter), an electrodermal sensor (e.g., a galvanometer), an auscultation sensor (e.g., a stethoscope, a blood pressure monitor), a blood-chemistry sensor (e.g., a glucose monitoring sensor, a ketone monitoring sensor), a load sensor (e.g., a weight scale sensor), a barometric pressure sensor (e.g., a barometer, an altimeter), a wave-detection sensor (e.g., a lidar sensor, a radar sensor, a sonar sensor), a gas sensor (e.g., a chromatography sensor, a smoke detector, an alcohol sensor, a dust particle sensor), and/or a water sensor (e.g., a chemical sensor, a turbidity sensor, a flow meter).

Input user device 222 may include, for example, a touchpad, a touch screen, a keyboard, a mouse, a button, a dial, a knob, a switch, a microphone, a camera, a video camera, a fingerprint scanner, an eye scanner, near field communication sensor, an RFID tag scanner, a smart card reader, and/or an ultrasonic scanner.

Output user device 223 may include, for example, a visual display (e.g., display 224), a light (e.g., a frequency or color-controlled light), a speaker (e.g., speaker 225), a mechanical control line, an electrical control line, a software control line, a radio control band (e.g., ISM, WIFI, BLUETOOTH), a broadcast radio band (e.g., emergency broadcast, FM, VHF, UHF, and/or a haptic feedback device (e.g., a vibration motor).

Display 224 may include, for example, a light-emitting display (e.g., a light emitting diode (LED) display, a lamp), a liquid-crystal display (LCD), a touch screen, and/or a projector.

Speaker 225 may include, for example, a wired speaker and/or a wireless speaker.

Microphone 226 may include, for example, a wired headset, a wired microphone, a wireless headset, and/or a wireless microphone.

Battery 227 may include, for example, a lithium-ion battery, a lithium battery, a large capacitor, a silver-oxide battery, a lead-acid battery, an alkaline battery, a zinc-air battery, and/or a nickel-cadmium battery. In some embodiments, battery 227 may be a rechargeable battery. In some embodiments, battery 227 may be a disposable battery. In some embodiments, battery 227 may be configured to provide approximately constant voltage (e.g., 3 volts, 9 volts, 12 volts) to user device 102.

In some embodiments, battery 227 may have a battery life that changes based on operations performed by user device 102 and/or based on device settings of user device 102. In some embodiments, the battery life of battery 227 may be extended if, for example, processor 210 performs fewer operations, memory 230 management needs are reduced, or I/O unit 220 demands are reduced. In some embodiments, the processor, memory, and I/O units do not affect each other directly. In some embodiments, the battery life of battery 227 may be shortened if, for example, processor 210 performs more operations, memory 230 management needs increase, or I/O unit 220 demands increase. In some embodiments, the battery life of battery 227 may be extended by placing user device 102, processor 210, I/O unit 220, and/or memory 230 in a sleep mode. In some embodiments, the battery life of battery 227 may be shortened or extended by adjusting I/O unit 220, sensor 221 (e.g., enabling or disabling, or by adjusting a frequency and/or a type of data collection), input device 222 (e.g., disabling specific interrupts when multiple conditions do not exist, such as not processing a volume down action when a volume is at 0 or off), output device 223 (e.g., disabling a cellular radio or WIFI from synchronizing with a server when new sensor data 221 does not exist), display 224 (e.g., by adjusting a display brightness, or the responsiveness to enable or disable when a subject is present versus absent), speaker 225 (e.g., by adjusting a loudness, by disabling the audio amplifier circuit when the volume is reduced to 0 or off), and/or transceiver 228 (e.g., by adjusting bandwidth usage, by disabling a radio to reduce interrupts that drive memory 230 and processor usage 210).

Transceiver 228 may include, for example, a WI-FI transceiver, a LI-FI transceiver, a Near Field Communication (NFC) transceiver, a radio transceiver, an ultra-high frequency (UHF) transceiver, a BLUETOOTH transceiver, an infrared transceiver, and/or a transceiver configured to connect with a cellular data network. In some embodiments, transceiver 228 may be configured to receive and/or transmit data according to a limited bandwidth (e.g., via channel).

Memory 230 may include, for example, volatile memory, non-volatile memory, magnetic memory, semiconductor memory, optical memory, removable memory, and/or non-removable memory. Memory 230 may include, for example, storage and/or non-transitory tangible computer-readable media. In some embodiments, memory 230 may include software that can be integrated into a computer system, non-transitory tangible computer-readable media, and/or existing communications software. In some embodiments, memory 230 may include an operating system for performing operations when executed by one or more processors.

In some embodiments, memory 230 may include a program (e.g., program 231). The program may include, for example, modules, codes, scripts, and/or algorithms. In some embodiments, a program is written in one or more programming languages and/or scripting languages. In some embodiments, a program may be implemented and/or replicated as firmware or circuit logic. In some embodiments, a program collects data via I/O unit 220. Some embodiments may use a type of memory that can have a larger or lesser drain on battery and processor for continued upkeep and refresh cycles within the circuit design. Some embodiments may use a type of memory that has an extended or limited number of reads or writes until memory failure occurs and power demand is impacted. In some embodiments, a program transmits data over a network and/or a direct connection, authenticates a subject, creates and/or edits a subject profile, records and/or analyzes voice data, captures image data, records and/or analyzes video data, detects fingerprints, receives and/or transmits data, displays or plays a message, generates haptic feedback, and/or stores data.

In some embodiments, memory 230 may include data (e.g., data 232). In some embodiments, data may be encrypted and/or unencrypted. In some embodiments, data may be collected using I/O unit 220. In some embodiments, data may include metadata and/or device data (e.g., one or more device settings). In some embodiments, data may include one or more databases comprising an organized or structured collection of tables, queries, objects, schema, reports, and/or views.

Figure 3:
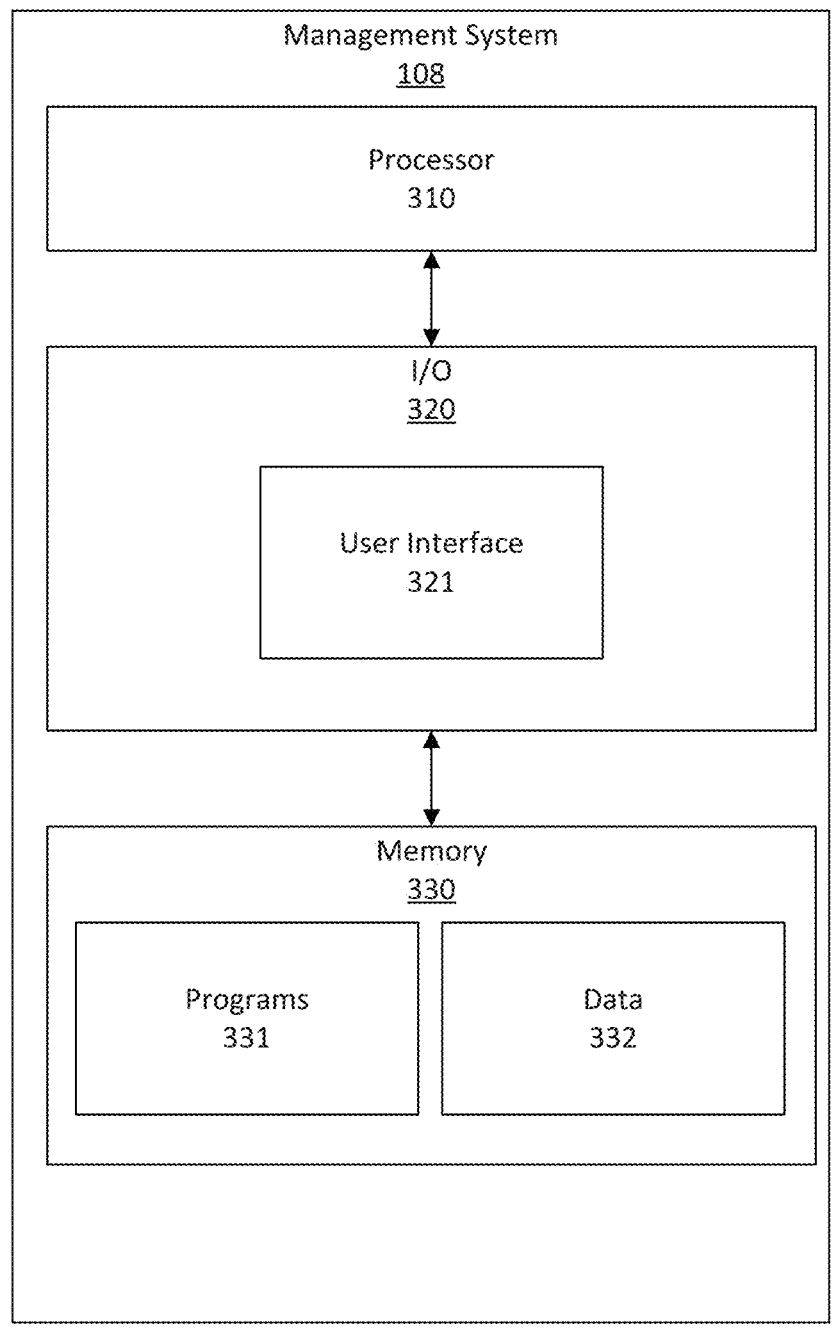
FIG. 3 is a diagram of an exemplary management system, consistent with disclosed embodiments.

FIG. 3 is a diagram of an exemplary management system 108, consistent with disclosed embodiments. Management system 108 may include one or more components. Management system 108 may include, for example, a processor 310, an I/O unit 320, and a memory 330. Management system 108 may include one or more of each component, it may include only some of these components, and it may include other components not depicted in FIG. 3. Components of management system 108 may be arranged in various ways.

Processor 310 may be, for example, a computing processor. In some embodiments, processor 310 may be a microprocessor. Processor 310 may be, for example, a single-core processor or a multiple-core processor (e.g., dual core, quad core). In some embodiments, processor 310 may include a single-core processor configured with virtual processing technologies. In some embodiments, processor 310 may include logical processors to simultaneously execute and control multiple processes. Processor 310 may implement technologies such as virtual-machine technologies to execute, control, run, manipulate, and/or store multiple processes, applications, and/or programs. In some embodiments, processor 310 may include a multiple-core processor configured to provide parallel processing functionalities for execution of multiple processes simultaneously. Processor 310 may be configured, for example, to execute one or more instructions stored in memory 330 to perform operations.

I/O unit 320 may include, for example, a user interface 321. In some embodiments, I/O unit 320 may be part of management system 108. In some embodiments, I/O unit 320 may be part of a separate device that is connected to management system 108. In some embodiments, I/O unit 320 may include one or more components connected to network 110. In some embodiments, I/O unit 320 may receive data from and/or transmit data to one or more components of system 100.

User interface 321 may include, for example, a display, an LED, a touchscreen, a keyboard, a microphone, a speaker, a haptic device, a camera, a button, a dial, a switch, a knob, an input device, and/or an output device. In some embodiments, user interface 321 may include components for receiving inputs and/or generating and displaying an interface as depicted in FIGS. 9, 10, and/or 11.

Memory 330 may include, for example, volatile memory, non-volatile memory, magnetic memory, semiconductor memory, optical memory, removable memory, and/or non-removable memory. Memory 330 may include, for example, storage and/or non-transitory tangible computer-readable media. In some embodiments, memory 330 may include software that can be integrated into a computer system, non-transitory tangible computer-readable media, and/or existing communications software. In some embodiments, memory 330 may include an operating system for performing operations when executed by one or more processors.

In some embodiments, memory 330 may include a program (e.g., program 331). The program may include, for example, modules, codes, scripts, and/or algorithms. In some embodiments, a program is written in one or more programming languages and/or scripting languages. In some embodiments, a program may be implemented and/or replicated as firmware or circuit logic. In some embodiments, a program collects data via I/O unit 320. In some embodiments, a program transmits data over a network and/or a direct connection, authenticates a user, creates and/or edits a user profile, records and/or analyzes data, receives and/or transmits data, displays or plays a message, and/or stores data.

In some embodiments, memory 330 may include data (e.g., data 332). In some embodiments, data may be encrypted and/or unencrypted. In some embodiments, data may be collected using I/O unit 320. In some embodiments, data includes metadata. In some embodiments, data may include data associated with a user, a user device, a remote device, a sensor, a sensor management system, a user account, and/or a group account. In some embodiments, data may include one or more databases comprising an organized or structured collection of tables, queries, objects, schema, reports, and/or views.

Figure 4:
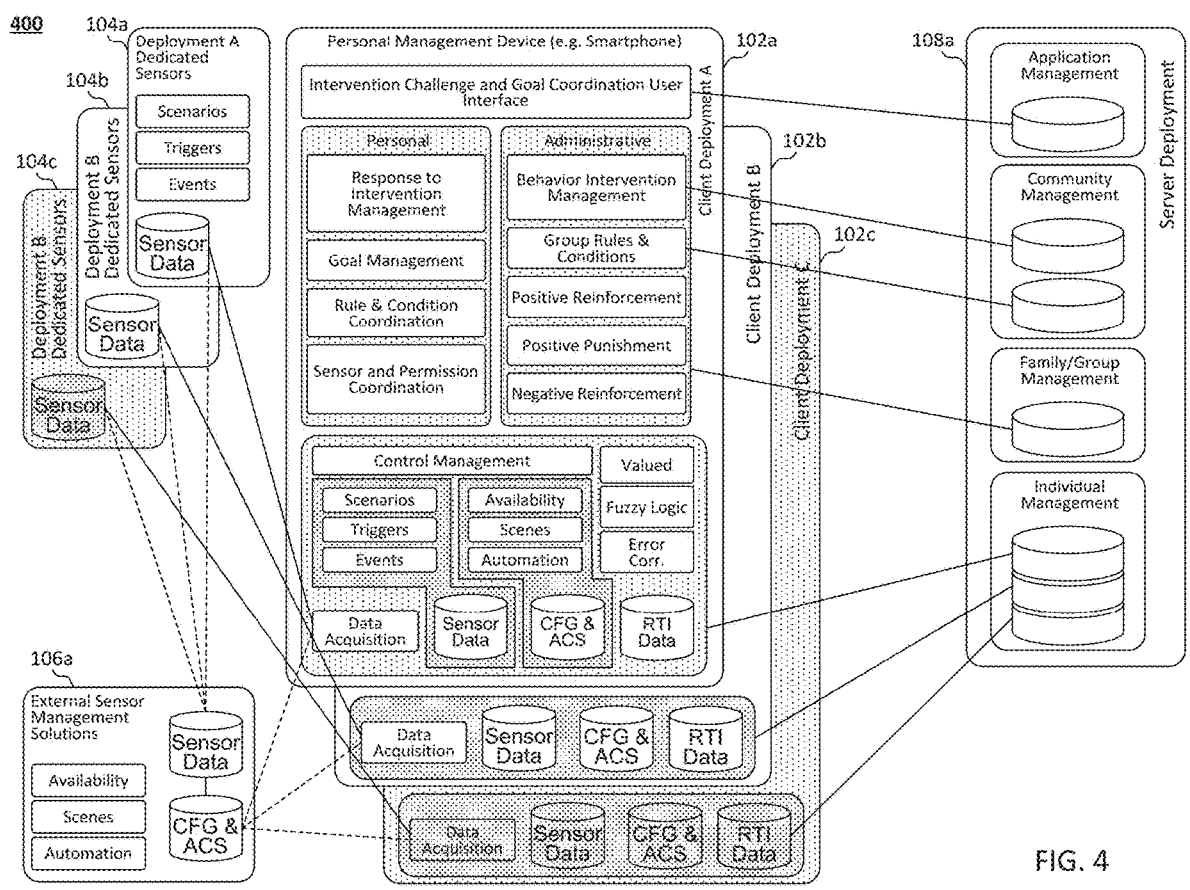
FIG. 4 is a diagram of an exemplary system for managing a measurement goal and performing an intervention, consistent with disclosed embodiments.

FIG. 4 is a diagram of an exemplary system 400 for managing a measurement goal and performing an intervention, consistent with disclosed embodiments. System 400 is shown for purposes of illustration only and is not limiting on the embodiments. System 400 is an exemplary embodiment of system 100.

As shown, system 400 may include a plurality of user devices 102a, 102b, and 102c. System 400 may include a plurality of remote devices 104a, 104b, and 104c. System 400 may include an external sensor management solutions system 106a. System 400 may include a management system 108a. The arrangement of components of system 400 is illustrative only and not intended to be limiting on the embodiments. For example, as compared to the illustration in FIG. 4, an embodiment of system 400 may include more or fewer of each component, it may include only some of these components, and it may include other components not depicted in FIG. 4.

User devices 102a, 102b, and 102c may be examples of user device 102, consistent with disclosed embodiments. FIG. 4 illustrates aspects of user device 102a as described herein, and one of skill in the art would appreciate that other user devices, such as user device 102b and 102 may include such aspects. As shown, user device 102a may be a personal management device configured to generate and display a user interface. The user interface may be capable of receiving and providing data. Data may relate to a management goal. Data may relate to an intervention.

Remote devices 104a, 104b, and 104c may be examples of remote device 104, consistent with disclosed embodiments. Remote devices 104a, 104b, and 104c may include one or more memory units for storing instructions and one or more processors for executing the instructions to perform operations. As previously described in reference to the remote device 104 of FIG. 1, remote devices 104a, 104b, and 104c may include any computing component. For example, remote devices 104a, 104b, and 104c may include a mobile device, a fitness-tracking device, a computer, a tablet device, a kiosk, a hub, a set top box, a digital assistant, an internet television device, a personal wearable device, an internet-of-things (loT), or a device configured to perform operations. Remote devices 104a, 104b, and 104c may include one or more sensors. Remote devices 104a, 104b, and 104c may include an access device, consistent with disclosed embodiments. Remote devices 104a, 104b, and 104c may include data relating to a scenario, a trigger, and/or an event, consistent with disclosed embodiments. Remote devices 104a, 104b, and 104c may include sensor data.

External sensor management solutions system 106a may be an example of sensor management system 106. Sensor management solutions system 106a may include hardware, software, and/or firmware. Sensor management solutions system 106a may include one or more memory units for storing instructions and one or more processors for executing the instructions to perform operations. As previously described in reference to sensor management system 106 of FIG. 1, sensor management solutions system 106*a* may include a personal computer, a server, a server cluster, and/or a cloud service. Sensor management solutions system 106*a* may include data storage. Sensor management solutions system 106*a* may include a Configuration Server (CFG) and/or an Access Control Server (ACS). Sensor management solutions system 106*a* may include sensor data, data relating to availability of a remote device, data relating to scenes, and/or data relating to automation.

Management system 108*a* may be an example of management system 108. Management system 108*a* may include hardware, software, and/or firmware. Management system 108*a* may include one or more memory units for storing instructions and one or more processors for executing the instructions to perform operations. In some embodiments, management system 108*a* may include a personal computer, a server, a server cluster, and/or a cloud service. Management system 108*a* may include data storage. Management system 108*a* may be configured for application management, user account management, group management, and individual management of measurement goals and/or interventions. Management system 108*a* may be configured to manage data collection across a plurality of user devices, remote devices, and sensor management systems. Management system 108*a* may be configured to manage an intervention across a plurality of user devices, remote devices, and sensor management systems.

As illustrated by solid and dashed lines in FIG. 4, components of system 400 may be connected to one another and may be configured to exchange data. For example, components of system 400 may be connected via a network, such as network 110, consistent with disclosed embodiments. Components of system 400 may be directly connected to one another via a wired or wireless connection, consistent with disclosed embodiments.

Figure 5:
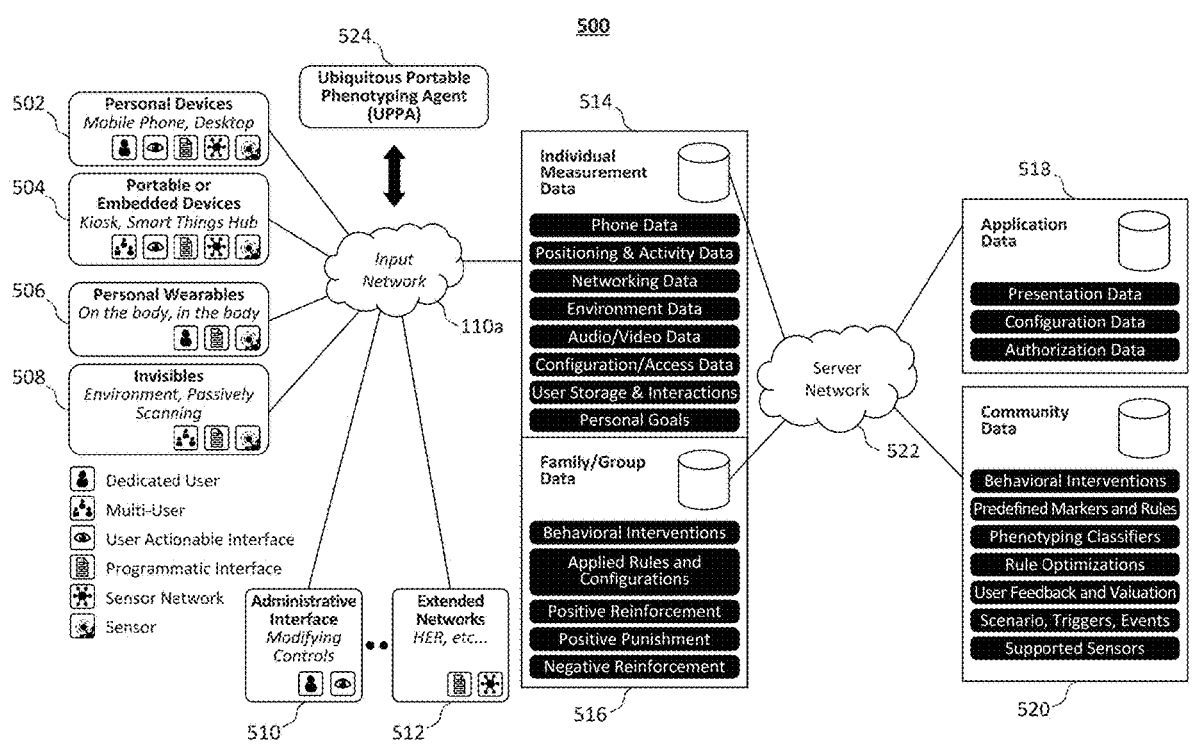
FIG. 5 is a diagram of an exemplary data network for managing a measurement goal and performing an intervention, consistent with disclosed embodiments.

FIG. 5 is a diagram of exemplary data network 500 for managing a measurement goal and performing an intervention, consistent with disclosed embodiments. As shown in FIG. 5, data network 500 may include a plurality of data storage locations for various data. Data network 500 may include one or more personal device storages 502, one or more portable or embedded device storages 504, one or more personal wearable storages 506, one or more invisible device storages 508, an individual measurement data storage 514, a family or group data storage 516, an application data storage 518, a community data storage 520. Data network 500 may include components for managing data storage and data transfer, including a ubiquitous portable phenotyping agent 524, an administrative interface 510, and one or more extended networks 512. As shown, components of data network 500 may be connected by one or more networks.

One or more components data network 500 may connect to input network 110*a*. In some embodiments, input network 110*a* may be a component of network 110. In some embodiments, input network 110*a* is network 110. Data may flow between components in any direction in input network 110*a*. In some embodiments, input network 110*a* may be a public network or a private network and may include, for example, a wired network or a wireless network. In some embodiments, input network 110*a* may be a local area network (LAN), a wide area network (WAN), a metropolitan area network (MAN), an IEEE 802.11 wireless network, a WI-FI network, a network of networks, the Internet, and/or a land-line telephone network. In some embodiments, input network 110*a* may be a secure network, for example, requiring a password or authentication for access.

One or more components data network 500 may connect to server network 522. In some embodiments, server network 522 may be a component of network 110. Data may flow between components in any direction in server network 522. In some embodiments, server network 522 may be a public network or a private network and may include, for example, a wired network or a wireless network. In some embodiments, server network 522 may be a local area network (LAN), a wide area network (WAN), a metropolitan area network (MAN), an IEEE 802.11 wireless network, a WI-FI network, a network of networks, the Internet, and/or a land-line telephone network. In some embodiments, server network 522 may be a secure network, for example, requiring a password or authentication for access.

The arrangement of components of system 500 is illustrative only and not intended to be limiting on the embodiments. For example, as compared to the illustration in FIG. 5, an embodiment of system 500 may include more or fewer of each component, it may include only some of these components, and it may include other components not depicted in FIG. 5.

As shown by the exemplary icons depicted in FIG. 5, data stored on components of system 500 may have various data labels or classifications provided in the legend. For example, data may be labelled as viewable and/or editable for dedicated to a user (i.e., viewable by a single authorized user). Data may be labelled as viewable and/or editable for multiple users. Data may be labelled as configured for a user actionable interface (i.e., a user interface). Data may be labelled as configured for a programmatic interface that allows interventions to be selected, configured and shared to a group and allows for data to be provided to a group. In some embodiments, data may be labelled as being collected by a sensor network. Data may be labelled as being collected by a particular sensor. The labels provided in FIG. 5 are not limiting on the embodiments and other embodiments may include additional, fewer, or different labels than those depicted in data network 500.

Personal device storage 502 may include a data storage of user device 102. In some embodiments, a personal device may include a mobile phone, a desktop, or other user device. In some embodiments, personal device storage 502 may be embedded in user device 102. In some embodiments, personal device storage 502 may store data received from user device 102. In some embodiments, personal device storage 502 may include a database. Personal device storage 502 may be connected to input network 110*a* and/or any other network.

Portable or embedded device storage 504 may include a data storage of remote device 104. In some embodiments, portable or embedded device storage 504 may include a kiosk, a smart things hub, or an IoT device. In some embodiments, portable or embedded device storage 504 may be embedded in remote device 104. In some embodiments, portable or embedded device storage 504 may store data received from remote device 104. In some embodiments, portable or embedded device storage 504 may include a database. Portable or embedded device storage 504 may be connected to input network 110*a* and/or any other network.

Personal wearable device storage 506 may include a data storage of a user device 102 or a remote device 104. For example, personal wearable device storage 506 may include storage of a device worn on a person, attached to a person, or embedded in a person. In some embodiments, personal wearable device storage 506 may be embedded in user device 102 or remote device 104. In some embodiments, personal wearable device storage 506 may store data received from user device 102 or remote device 104. In some embodiments, personal wearable device storage 506 may include a database. Personal wearable device storage 506 may be connected to input network 110a and/or any other network.

Invisible device storage 508 may include a data storage of remote device 104. In some embodiments, invisible device storage 508 may include a data storage of a remote device comprising a passive sensor, such as an environmental sensor. In some embodiments, invisible device storage 508 may be embedded in remote device 104. In some embodiments, invisible device storage 506 may store data received from remote device 104. In some embodiments, invisible device storage 508 may include a database. Invisible device storage 508 may be connected to input network 110a and/or any other network.

Data network 500 may include individual measurement data storage 514 for storing data associated with an individual user. For example, individual measurement data storage 514 may include phone data, positioning and activity data, networking data, environmental data, audio/video data, configuration data, access data, user storage and interactions data (e.g., memory used, data views), personal goal data, or other data. In some embodiments, individual measurement data storage 514 may be a component of management system 108. In some embodiments, individual measurement data storage 514 may include a database. Individual measurement data storage 514 may be connected to network input 110a, server network 522, and/or any other network.

Data network 500 may include family or group data storage 516 for storing data associated with a family or group. For example, family or group data storage 516 may include intervention data, rules and configuration data, positive reinforcement data, negative reinforcement data, or other data. In some embodiments, family or group data storage 516 may be a component of management system 108. In some embodiments, family or group data storage 516 may include a database. Family or group data storage 516 may be connected to input network 110a, server network 522, and/or any other network.

Data network 500 may include application data storage 518 for storing data associated with an application or a deployment of an application. For example, application data storage 518 may include presentation data, configuration data, authorization data, or other data. In some embodiments, application data storage 518 may be a component of management system 108. In some embodiments, application data storage 518 may include a database. Application data storage 518 may be connected to input network 110a, server network 522, and/or any other network.

Data network 500 may include community data storage 520. For example, community data storage 516 may include intervention data, marker data, rule data, phenotyping classifier data (e.g., data classifying individual behavior or characteristics), rule optimizations data (e.g., data related to training and optimizing rules), user feedback and valuation data, scenario data, trigger data, event data, supported sensor data, or other data. In some embodiments, community data storage 520 may be a component of management system 108. In some embodiments, community data storage 520 may include a database. Community data storage 520 may be connected to input network 110a, server network 522, and/or any other network.

Data network 500 may include an administrative interface 510. Administrative interface 510 may be configured to allow a user to view data, edit data, and manage data collection. Administrative interface 510 may include an interface of user device 102, sensor management system 104, or management system 108. Administrative interface 510 may be configured to manage device settings (e.g., remote device settings, user device settings) and/or sensor settings. Administrative interface 510 may be configured to generate or track a measurement goal and/or an intervention.

Data network 500 may include an interface to transmit data to or receive data from one or more outside network (extended networks 512). For example, extended networks 512 may include an electronic health record (EHR) system.

Data network 500 may include a ubiquitous portable phenotyping agent 524 for managing data across data network 500. In some embodiments, ubiquitous portable phenotyping agent 524 may be a component of user device 102, such as a program or software application installed on user device 102 (e.g., an app). In some embodiments, ubiquitous portable phenotyping agent 524 may be a component of management system 108. For example, ubiquitous portable phenotyping agent 524 may be a program deployed on a server.

FIG. 6 is a diagram of exemplary data structure 600 for managing a measurement goal and performing an intervention, consistent with disclosed embodiments. Data of data structure 600 may be stored in, for example, a data storage of user device 102, remote device 104, sensor management system 106, management system 108, or another data storage. Data of data structures 600 may be stored in a database.

FIG. 6 depicts an organizational structure (data structure 600) of data of the embodiments and is provided for purposes of illustration and is not limiting on the embodiments. Data of the embodiments may be stored in data structures other than data structure 600. Data structures of the embodiments may include data labels, data classifications, and organizational relationships that differ from those depicted in FIG. 6.

As shown, data of data structure 600 may be classified as behavioral intervention data 602, applied rules and configuration data 604, and recipient measurement data 606. Data structure 600 may include other data classifications, not depicted.

Behavioral intervention data 602 may include data labelled according to one or more behavioral use cases. For example, as shown, behavior use cases may include data labelled as suitable for a behavior use case of anxiety, loneliness, attention deficit disorder, loss of appetite, boredom, mental health, depression, social avoidance, disrupted sleeping, stress, fatigue, improved work/life balance, or other behavior use cases. Behavioral intervention data 602 may include machine learning model data, statistical model data, or other model data. For example, behavioral intervention data 602 may include parameters of a model. Behavioral intervention data 602 may include one or more logical expressions, including a combination of expressions. Expressions may be associated with a measurement goal or a marker. Behavioral intervention data 602 may include analysis results based on sensor data. The analysis result may indicate whether a measurement goal or marker has been satisfied.

Applied rules and configurations 604 may include feature classification data. Feature classification data may be associated with a measurement goal or a marker. For example, feature classification data may include rules (e.g., models, logical expressions) to determine whether a condition is met. Feature classification data may include processed data indicating whether a condition is met. In some embodiments, the condition may include whether: a user is actively checking a phone; a user is actively visiting (using) an app; a user is rapidly changing apps; a user is using a fidget spinner; a user's biomarkers are changing; an environment has a sudden change; a user is pacing; a battery is rapidly depleting; a phone is intensely used; a user is avoiding social interactions; a social proximity is increasing; a user is watching television; a user has not moved; a user's typing accuracy has decreased; a user is shaking; a user is sleeping; a user is commuting; a user is sleeping well; a user's sleep is interrupted; a user is eating; a user is engaged in conversation; a user is actively moving; weather is altering a mood; or any other condition is satisfied.

Recipient measurement data 606 may include data classified according to a sensor type and/or a sensor. A sensor type may include audio/video, networking, phone, environment, positioning and activity, user storage and interactions, or any other sensor type. Data classified as audio/video sensor type may include data classified as raw audio data, audio noise classifier data, audio transcript data, ambient sound level data, microphone state data, speaker level data, speaker control adjustment data, audio filtering data, or other audio/video data. Data classified as networking sensor type data may include data classified as a BLUETOOTH state, a BLUETOOTH nearby device list, a network state, a telephony state, a WI-FI state, a WI-FI nearby list, a call log, a phone usage, or any other networking data. Data classified as phone sensor type data may include data classified as app class data, app name data, app usage data, app state data, battery level data, battery state data, Simple Messaging System (SMS) content data SMS log data, or any other phone data. Data classified as environment sensor type data may include data classified as barometer data, camera image detection data, camera light wavelength data, ambient light level data, proximity data, temperature data, processor usage data, semantic time data, or any other environment data. Data classified as positioning and activity sensor type data may include data classified as accelerometer data, altimeter data, Global Position System data, gravity data, gyroscope data, linear accelerometer data, location classification data, user acceleration data, or any other positioning and activity data. Data classified as user storage and interaction sensor type data may include data classified as keyboard data, screen data, touch data, touch pattern data, user health storage data, time zone data, magnetometer data, rotation data, or any other user storage and interaction data.

Figure 7:
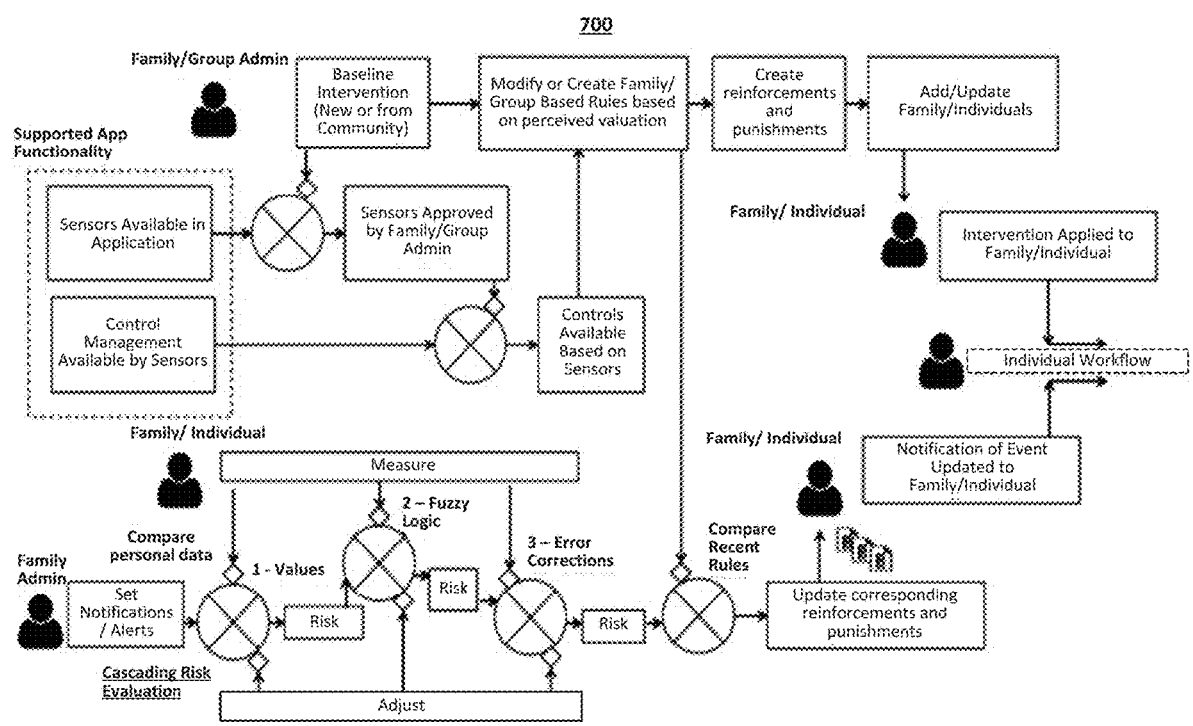
FIG. 7 is a diagram of an exemplary workflow for an administrator of a group, consistent with disclosed embodiments.

FIG. 7 is a diagram of an exemplary workflow 700 for an administrator of a group, consistent with disclosed embodiments. A group may include a family, a team, or any other group.

Figure 8:
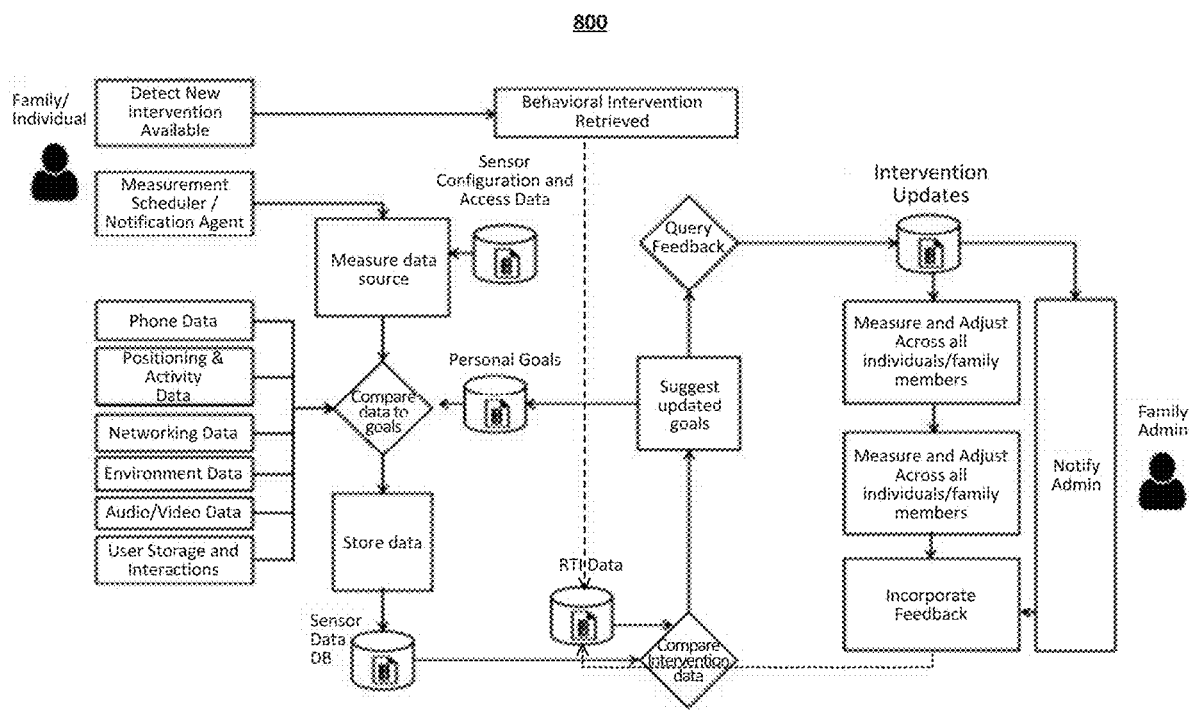
FIG. 8 is a diagram of an exemplary workflow for a user, consistent with disclosed embodiments.

FIG. 8 is a diagram of an exemplary workflow 800 for a user, consistent with disclosed embodiments.

FIG. 9 is a diagram of exemplary user interfaces 902 and 904 displaying user views, consistent with disclosed embodiments. User interfaces 902 and/or 904 may be displayed on a display of user device 102. In some embodiments, user interfaces 902 and/or 904 may be displayed on a display of remote device 104, sensor management system 106, management system 108, or any other display. User interfaces 902 and 904 are provided for purposes of illustration only and are not limiting on the embodiments. Embodiments may include other user interfaces than those depicted in FIG. 9. User interfaces 902 and 904 may include interactive features configured to display additional information or perform an action in response to user input such as in response to a touch screen input or a mouse input or a click.

User interface 902 may include an interface associated with an individual user or an administrator. As shown, interface 902 may include interactive features relating to a compare function, a goal function related to a measurement goal, a dashboard function, a settings function, or a manage intervention function.

User interface 904 may include an interface associated with an administrator. As shown, interface 904 may include interactive features relating to a configure function, a dashboard function, an import function, a create function, a settings functions, or a start on this screen function.

FIG. 10 is a diagram of exemplary user interfaces 1002 and 1004 displaying administrator views, consistent with disclosed embodiments. User interfaces 1002 and/or 1004 may be displayed on a display of user device 102. In some embodiments, user interfaces 1002 and/or 1104 may be displayed on display of remote device 104, sensor management system 106, management system 108, or any other display. User interfaces 1002 and 1004 are provided for purposes of illustration only and are not limiting on the embodiments. Embodiments may include other user interfaces than those depicted in FIG. 10. User interfaces 1002 and 1004 may include interactive features configured to display additional information or perform an action in response to user input such as in response to a touch screen input or a mouse input or a click.

User interface 1002 may include an interface associated with configuring an intervention. As shown, user interface 1002 may include interactive features relating to an on/off function, a configure function for a rule (e.g., "Rule N," "Rule N+1"), a configure function for a value (e.g., "Value N," "Value N+1"), a configure function for a reward (e.g., "Reward N," "Reward N+1"), a monitor progress function, a review feedback function, and a manage family/individual function.

As illustrated in FIG. 10 by the dashed lines and arrow, when a configure "Rule N" or configure "Rule N+1" is selected, user interface 1004 may be provided. As shown, user interface 1004 may include an on/off function, a coding function, an update function, a test function, and a list events function. A coding function may include a series of instructions written in code comprising check statements, when statements, while statements, do statements, Boolean logical statements, or the like.

Figure 11:
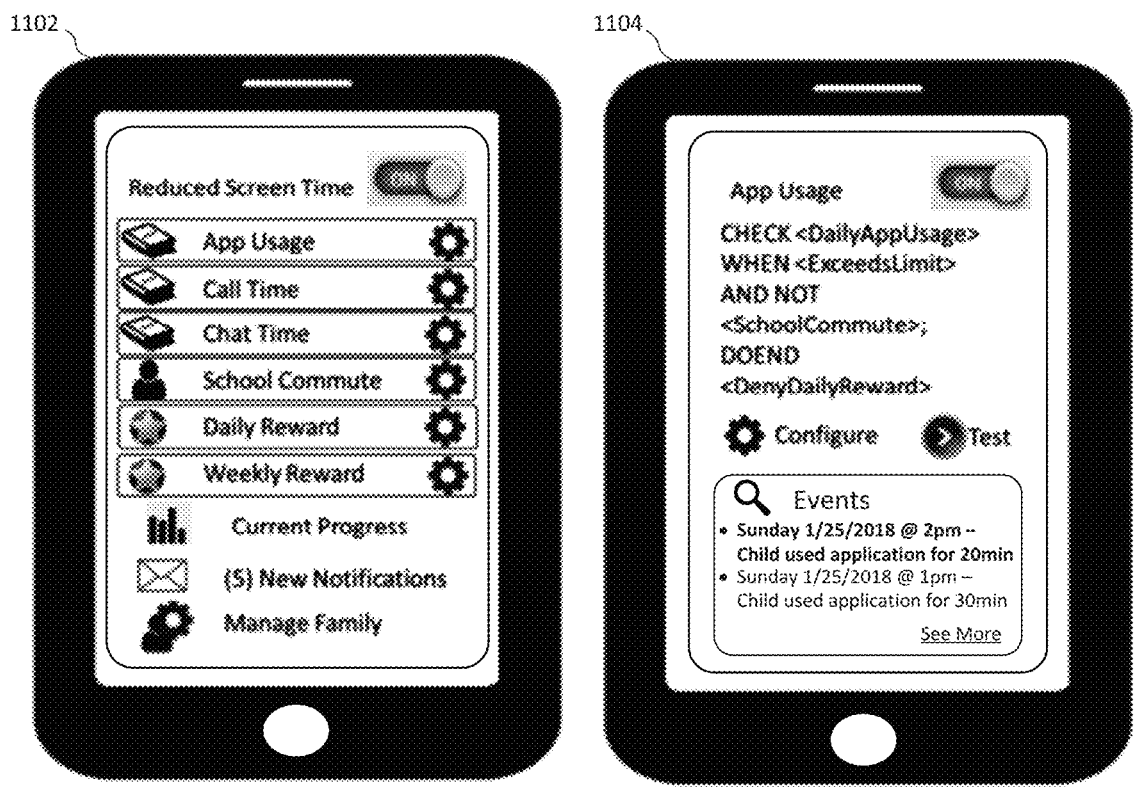
FIG. 11 is a diagram of exemplary user interfaces during an intervention, consistent with disclosed embodiments.

FIG. 11 is a diagram of exemplary user interfaces 1102 and 1104 during an intervention, consistent with disclosed embodiments. User interfaces 1102 and 1104 may be displayed on user device 102, remote device 104, sensor management system 116, management system 118, or any other display. User interfaces 1102 and 1104 are provided for purposes of illustration only and are not limiting on the embodiments. Embodiments may include other user interfaces than those depicted in FIG. 11. User interfaces 1102 and 1104 may include interactive features configured to display additional information or perform an action in response to user input such as in response to a touch screen input or a mouse input or a click.

User interface 1102 may include an interface associated with intervention to reduce user screen time. As shown, user interface 1102 may include interactive features relating to turning a measurement goal for reduced screen time on or off (i.e., enabling a measurement goal), app usage settings, call time settings, chat time settings, school commute settings, daily reward settings, weekly reward settings, a current progress function, a notification function, and a manage family setting.

User interface 1104 may include an interface associated with an app usage setting. For example, user interface 1104 may be displayed after receiving inputs that select an app usage setting of user interface 1102. As shown, user interface 1104 includes a coding function, a configure function, a test function, and an events reporting function. A coding function may include a series of instructions written in code comprising check statements, when statements, while statements, do statements, Boolean logical statements, or the like. As depicted in exemplary user interface 1104, a coding function may restrict app usage by, for example, denying a daily reward when app usage exceeds a threshold or when an app is used while a user commutes to a school.

Figure 12:
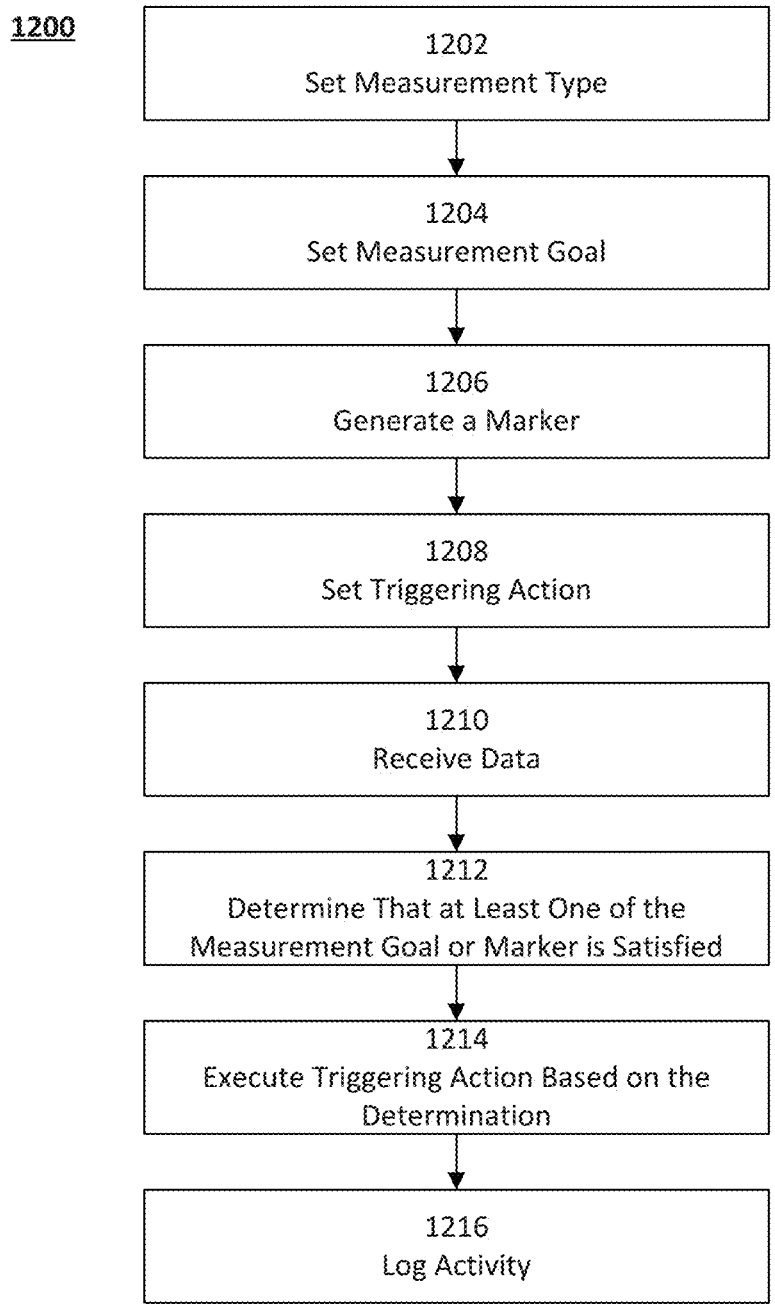
FIG. 12 is a diagram of an exemplary process for managing an intervention, consistent with disclosed embodiments.

FIG. 12 is a diagram of exemplary process 1200 for managing an intervention, consistent with disclosed embodiments. In some embodiments, user device 102 may perform steps of process 1200. In some embodiments, one or more of remote device 104, sensor management system 106, management system 108 may perform steps of process 1200 with or without user device 102.

At step 1202, user device 102 may set a measurement type, consistent with disclosed embodiments. In some embodiments, a measurement type may be related to a behavior and/or a health status. A measurement type related to a behavior may include an internet usage, a screen time, a video game usage, a social media usage, an exercise pattern, a diet, a sleep pattern, a medication adherence, or any other behavior. A measurement type be related to a health status may include a body mass index, a heart rate measure, a breathing measure, a blood pressure measure, a hydration measure, a sleep quality score, an anxiety score, a depression score, or any other health indicator.

In some embodiments, a measurement type may include identifying one or more users (e.g., one or more group members such as a family members or team members). Setting a measurement type may include identifying one or more remote devices (e.g., remote device 104). In some embodiments, setting a measurement type may include identifying one or more user devices (e.g., user device 102).

At step 1204, user device 102 may set a measurement goal, consistent with disclosed embodiments. In some embodiments, a measurement goal may be based on a measurement type. In some embodiments, a measurement goal may relate to a behavior or a health status. For example, a measurement goal may include a threshold (i.e., a minimum or a maximum) of an indicator of a behavior or a health status. Examples of measurement goals may include a minimum number of hours spent studying during a week, a maximum anxiety score, a resting heart rate threshold, a maximum screen time, a minimum number of social interactions, a vegetables-consumed threshold, a medication adherence minimum, and/or any other threshold of an indicator of a behavior or health status.

In some embodiments, setting a measurement goal may include generating a coding function. A coding function may include check statements, when statements, while statements, do statements, Boolean logical statements, or the like. A coding function may calculate an indicator of a behavior or a health status based on data received from user device 102 and/or remote device 104, consistent with disclosed embodiments. In some embodiments, a coding function may be based on sensor data.

In some embodiments, setting a measurement goal may include generating or retrieving a machine learning model trained to predict an indicator of behavior or health status. A machine learning model may include a neural network model, a recurrent neural network model, a random forest model, a support vector model, and/or any other machine learning model both unsupervised and supervised. In some embodiments, setting a measurement goal may include generating or retrieving a fuzzy logic model. A fuzzy logic model may be configured to estimate general truths. For example, a fuzzy logic model may be configured to determine that an indicator mostly satisfies a measurement goal, that an indicator is close to a threshold, and/or that an indicator is nearing a threshold.

In some embodiments, setting a measurement goal may include identifying one or more user devices, remote devices, and/or sensor management systems. In some embodiments, a measurement goal may include a threshold, a coding function, and/or a model based on data from a user device and/or a remote device. In some embodiments, a measurement goal may be associated with one or more users (e.g., an individual or one or more group members).

At step 1206, user device 102 may generate a marker related to a measurement goal, consistent with disclosed embodiments. In some embodiments, a marker may include a condition that may predict whether a measurement goal is likely to be satisfied in the future. For example, a maker may include an estimate of whether a student is likely to satisfy a measurement goal of studying for at least ten hours between a Monday and a Sunday based on a present cumulative number of hours spent studying (e.g., a number of hours spent studying as of Wednesday). As another example, a marker may be based on a coding function or model that accepts alcohol consumption data, motion data, and screen time data, as input and estimates whether a user is likely to meet a sleep quality score as output.

A marker may include a threshold, a coding function, a machine learning model, and/or a fuzzy logic model consistent with disclosed embodiments. A marker may include a statistical relationship between a measurement goal and a threshold, a coding function output, a machine learning model output, and/or a fuzzy logic model output. In some embodiments, a marker may be associated with one or more user devices and/or one or more remote devices. For example, a marker may include a threshold, a coding function, and/or a model based on data from a user device and/or a remote device. In some embodiments, a marker may be associated with one or more users (e.g., an individual or one or more group members).

Generating a marker may include receiving input data. For example, user device 102 may generate a marker based on input data received via I/O devices 220. The input data may include instructions to set a threshold, generate a coding function, train a machine learning model, and/or configure a fuzzy logic model, consistent with disclosed embodiments. In some embodiments, generating a marker may include performing steps of process 1300, below.

At step 1208, user device 102 may set a triggering action, consistent with disclosed embodiments. Setting a triggering action may be based on a marker. Setting a triggering action may be based on a measurement goal. In some embodiments, setting a triggering action may include generating an instruction to perform a triggering action when at least one of a measurement goal or a marker is satisfied. In some embodiments, setting triggering action may be based on input data (e.g., input data received via I/O devices 220).

A triggering action may include controlling access to a user device (e.g., user device 102 and/or another user device). For example, a triggering action may include preventing a user from unlocking a device, preventing a user from logging onto a device, locking a device, logging off a device, or the like.

A triggering action may include controlling access to an application of a user device (e.g., an application of user device 102 and/or another user device). For example, a triggering action may prevent a user from opening a social media app or allow a user to open a social media.

A triggering action may include controlling access by a user device to a network (e.g., user device 102 and/or another user device). For example, a triggering action may prevent a device from accessing a cellular data network or a WI-FI network.

A triggering action may include controlling access by a user device to a website (e.g., user device 102 and/or another user device). For example, a triggering action may prevent a user device from accessing a video streaming service.

A triggering action may include displaying a notification on the user device (e.g., user device 102 and/or another user device). For example, a notification may warn a user regarding whether the user is likely to meet a measurement goal. A notification may include a reward, an encouraging message, a reminder, or the like.

A triggering action may include transmitting a command to a remote device and/or a user device (e.g., remote device 104, user device 102, and/or another device). The command may comprise an instruction to control access to a physical space. For example, a triggering action may include unlocking a door such as an entertainment room door, a freezer door, a liquor cabinet door, or the like. The command may comprise an instruction to control access to the remote device, control access to an application, control access to a network, control access to a website, or the like.

At step 1210, user device 102 may receive data, consistent with disclosed embodiments. Receiving data may include receiving data from a component of user device 102, from another user device, from remote device 104, from sensor management system 106, from management system 108, and/or from a computing component outside system 100. In some embodiments, received data may include sensor data. For example, received data may comprise data collected by a sensor of user device 102, a sensor of another user device, a sensor of remote device 104, and/or any other sensor. As an illustrative example, user device 102 may be a parent's device and may receive data from a child's user device and from sensor management system 106, the data from sensor management system 106 comprising data collected from plurality of remote devices (e.g., IoT devices).

At step 1212, user device 102 may determine whether at least one of a measurement goal or a marker is satisfied, based on received data, consistent with disclosed embodiments. For example, user device 102 may compare data to a threshold, execute a coding function, implement a machine learning model, or implement a fuzzy logic model. To continue the illustrative example of the previous step, at step 1212, user device 102 may determine that a child has failed to meet a measurement goal (e.g., failed to meet an exercise goal).

At step 1214, user device 102 may execute a triggering action based on a determination that at least one of a measurement goal or a marker is satisfied. For example, user device 102 may execute a triggering action that includes controlling access to a user device, controlling access to an application of a user device, controlling access by a user device to a network, controlling access by a user device to a website, displaying a notification on the user device, transmitting a command to a remote device, the command comprising an instruction to control access to a physical space, and/or any other triggering action. To continue the illustrative example of the previous step, at step 1214, user device 102 may send a command to a device associated with the child based on a determination that a child failed to meet a measurement goal, the command comprising an instruction to prevent access to a video streaming service (e.g., NETFLIX video streaming).

At step 1216 user device 102 logs activity, consistent with disclosed embodiments. Logging activity may include generating a log file or updating a log file (e.g., appending log data). Logging activity may include storing received data. Logging activity may include storing information related to a measurement goal, a marker, and/or a triggering action. For example, logging activity may include storing whether a triggering action was executed.

Figure 13:
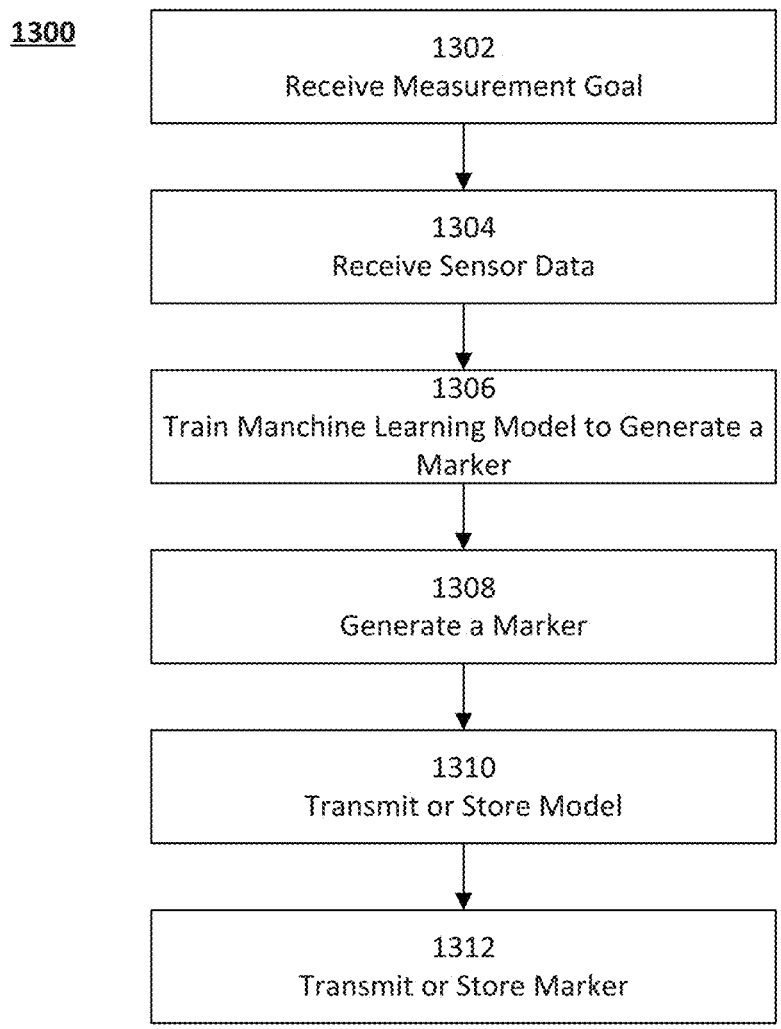
FIG. 13 is a diagram of an exemplary process for generating a marker, consistent with disclosed embodiments.

FIG. 13 is a diagram of exemplary process 1300 for generating a marker, consistent with disclosed embodiments. In some embodiments, process 1300 may be performed to adjust (i.e., update) an existing marker. In some embodiments, process 1300 may be performed to generate a new marker.

In some embodiments, user device 102 may perform steps of process 1300. In some embodiments, one or more of remote device 104, sensor management system 106, management system 108 may perform steps of process 1300 with or without user device 102.

At step 1302, management system 108 may receive a measurement goal, consistent with disclosed embodiments. As previously described, a measurement goal may relate to a behavior or a health status.

Receiving a measurement goal may include receiving a measurement goal from user device 102, from another component of system 100, and/or from a computing component outside system 100. Receiving a measurement goal may include receiving inputs via user interface 321 and/or from user device 102, the inputs comprising instructions to retrieve a stored measurement goal (e.g., from memory 330), to update a stored measurement goal, and/or to generate a measurement goal.

At step 1302, management system 108 may receive a marker, consistent with disclosed embodiments. As previously described, a marker may relate to a behavior or a health status.

Receiving a marker may include receiving a marker from user device 102, from another component of system 100, and/or from a computing component outside system 100. Receiving a marker may include receiving inputs via user interface 321 and/or from user device 102, the inputs comprising instructions to retrieve a stored marker (e.g., from memory 330), to update a stored marker, and/or to generate a new marker.

At step 1304, management system 108 may receive sensor data, consistent with disclosed embodiments. Receiving sensor data may include receiving sensor data from user device 102, remote device 104, and/or sensor management system 106. Receiving sensor data may include retrieving sensor data from storage (e.g., memory 330).

At step 1306, management system 108 may train a machine learning model, consistent with disclosed embodiments. In some embodiments, a machine learning model may be trained to receive sensor data as input and return an estimate of a likelihood that a future measurement goal may be satisfied. In some embodiments, a machine learning model may be trained to generate a marker comprising a coding function that receives sensor data as input and returns an estimate of a likelihood that a future measurement goal may be satisfied. In some embodiments, step 1306 may include adjusting a marker by training a model to update a maker based on received sensor data and implementing the trained model.

A machine learning model at step 1306 may include a neural network model, a recurrent neural network model, a random forest model, a support vector model, or any other machine learning model. In some embodiments, training a machine learning model may include training a fuzzy logic model. Training a machine learning model may be based on optimizing a loss function or other known training methods. Training may be supervised or unsupervised. Training a model may include generating a model based on a template. Training a model may include receiving input data specifying a model architecture (e.g., receiving input data from a component of system 100 and/or via interface 321). At step 1308, management system 108 may generate a marker, consistent with disclosed embodiments. For example, management system 108 may implement a trained model machine learning model to generate a marker comprising a coding function that receives sensor data as input and returns an estimate of a likelihood that a future measurement goal may be satisfied.

At step 1310, management system 108 may transmit or store a trained model, consistent with disclosed embodiments. Transmitting a trained model may include transmitting a model to user device 102, sensor management system 104, and/or a computing component outside system 100. Storing a trained model may include storing a model in memory 331.

At step 1312, management system 108 may transmit or store a marker, consistent with disclosed embodiments. Transmitting a marker may include transmitting a model to user device 102, sensor management system 104, and/or a computing component outside system 100. Storing a marker may include storing a model in memory 331.

EXAMPLES

Example 1: The Problem

In an illustrative example of an embodiment, an individual may have goal of increasing happiness and/or decreasing a level of depression. The individual may be aware that environmental factors and device use patterns precede depressive episodes but may be unable to accurately track data or prevent depressive episodes. For example, the user may know that increased internet browsing and decreased communication lead to depression but may be unable to detect or stop these behaviors.

Example 1: The Solution

To help detect and prevent depressive episodes, a management system 108 may collect active and/or passive data that may indicate conditions in the environment, individual behavior, and/or physiology. Such data may be collected in sousveillance and domotics to personalize goals related to behavioral shifts and provide interventions. As a result, a management system may aid in detecting, promoting and affirming positive and negative consequences to behavior.

The embodiment may help to track personalized markers while detecting behavior trends. And, much like a natural language processor, as more data is collected and analyzed, a management system 108 may learn and create knowledge of individual trends and patterns.

For example, a pattern may be detected when an individual reports himself or herself as depressed. The management system may determine that an individual adopts an identifiable pattern of use of apps (e.g., social media apps, streaming video apps, communication apps, productivity apps, game apps, and/or internet browsing apps) during a self-reported depressive episode. For example, the system may identify that, during self-reported depressive episodes, internet use increases while communication decreases. As another example, the system may detect a change in app usage such as decreased time playing a game previously associated with happiness markers, decreased time texting messages identified as "playful" on social interaction, increased time shopping, increased time aimlessly browsing the internet, etc.

The system may also learn to recognize behavior patterns that predict later behaviors or health statuses. As patterns are identified, machine learning may identify when patterns are likely to change. For example, the system may learn to predict a later depressive episode based on present changes in an environmental marker, daylight, a stress indicator, a loneliness indicator. The system may identify such predictors based on a statistically significant correlation. Accordingly, in the illustrative embodiment the system may monitor behaviors and suggest interventions when predictive trends are detected.

Interventions of the embodiment may include "a life coach," which may extend support through a virtual social group of real individuals connected to the a management system 108. In the embodiments, a group may create challenges (i.e., to set measurement goals collectively) and detect changes in moods, behavior patterns, or work with individual group members to virtually meet and provide support when help is needed.

Markers, such as depression, stress, or anxiety markers, may be computed in the embodiment at a local device level. In addition, management system 108 may generate population level metrics using data received by a plurality of devices associated with a plurality of individuals.

For example, using a management system (e.g., management system 108) the individual may join a self-help or depression therapy group. This group may be a group of cancer survivors, or any other group that helps support group members with health or behavior issues. The system may learn to identify baseline behavioral patterns of group members. The system may learn to monitor behavior and determine when an individual is likely to have an episode. The system may monitor and detect changes over any time period, including minutes, hours, days, weeks, or months.

The system may also learn to identify the likely impact of an intervention on an individual. For example, the system may correlate actions a "life coach" or a group member performs with a later health outcome or behavior pattern of an individual. Accordingly, the system may develop more effective interventions by learning the impact of actions such as sending messages to group members requesting help for a particular group member, giving a reward like a virtual medal, etc.

Example 2: The Problem

In another illustrative example of an embodiment, a family may have a goal of spending more time away from electronic devices, and more time together sharing experiences. The family believes that such devices are addictive. Family members may spend large amounts of time checking the news, playing a game, shopping, messaging friends, or the like. Family members may receive many notifications at random times on mobile phones related to these activities.

The notifications may provide short surges of pleasure and accompanying hormonal responses, leading to further addictive behavior regarding the use of electronic devices. The family would like to set a measurement goal that reduces their electronic device collectively, and individually.

To address these problems, a prescriptive tool may be required that may change the family members' behavior by reducing time spent on to regain time together. However, conventional approaches face challenges. Individuals may need to give consent to collect data from a mobile device. The device may need proper privacy, security, and enrollment protocols in a family group for sharing data. Family members may have different needs and may require customized solutions to address.

For example, Parent 1 may need to use a user device for business regularly between the hours of 5 am and 4 pm and irregularly at other hours for special cases (e.g., emergencies). Parent 1 may need unlimited data during office hours and limited data time after.

Parent 2 may need to use a user device to connect with friends and family, but not between the hours of 7 am and 5 pm while at work, unless there is an urgent issue. Parent 2 may wish to have access to certain news apps, personal email, and for an application to communicate with a childcare provider. Parent 2 may need only limited data at all times.

Child 1 may be in Junior-High School and may use a user device to connect with friends and family, personal email, school and productivity tools. Child 1 may also play games and watch videos but should not do so except between 7 pm and 8 pm. Child 1 may need unlimited data with restrictions on certain applications.

Child 2 may be in elementary school. Child 2 may use a user device for videos and playing games but should not do so except from 1 pm to 1:30 pm. Parent 1 and Parent 2 may use GPS on Child 2's phone to track Child 2's location.

The needs of the family members may vary over time based on work, holidays, school calendar, or the like.

Example 2: The Solution

Using a management system (e.g., management system 108), each family member may set individual measurement goals, while one or both of Parent 1 and Parent 2 may set measurement goals for the group, as a whole, and for Child 1 and Child 2. Family members may set measurement goals on user devices which are then propagated to other components of system 100.

For example, the system may set measurement goals related to screen time, use of particular applications, and data use. The system may set measurement goals related to sleep time (e.g., children must sleep between 9:30 pm until 6 am). The system may set measurement goals that restrict use based on a schedule and/or based on other conditions (e.g., when all family is in the house together).

The system may encourage positive behaviors by executing triggering actions. A triggering action may relate to notifications, to opening or closing an entertainment room that has a video game console, to controlling access to an application, or the like. For example, the system may send the children a reward such as reward tokens that give a random prize at 5 pm based on a weighting of percentage unused time, average aversion to screen usage, and focus on productivity and schooling versus games and videos. The parents may use their user devices to monitor performance and behaviors, confirm system approaches, and reward selections to ensure proper limits and weighting are being applied.

The system may help in managing a group of individuals jointly in achieving goals and intervention and the system may considering one or more individuals within a group. As previously described, the group may include any group of people, including, for example, individuals living in a home (such as a group of parents), a community group, a neighborhood group, a society, and/or a group of groups). For example, parents within a home may monitor each other by having their own customized interventions and goals along with a shared goal between them. The system may allow individuals to independently share goals, interventions, rewards, and/or other components of the system, such as sensors and sensor data in order to create group coordinated controls and/or configurations.

The foregoing description has been presented for purposes of illustration. It is not exhaustive and is not limited to precise forms or embodiments disclosed. Modifications and adaptations of the embodiments will be apparent from a consideration of the specification and practice of the disclosed embodiments. For example, while certain components have been described as being connected to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from a consideration of the specification and practice of the embodiments disclosed herein. It is intended that the specification and examples be considered as an example only, with a true scope and spirit of the disclosed embodiments being indicated by the following claims.

What is claimed is:

1. A system comprising:
one or more processors; and
one or more memory units storing instructions that are operable, when executed by the one or more processors, to cause the system to perform operations comprising:

receiving a measurement goal from a user device, the measurement goal relating to at least one of a behavior or a health status;

obtaining sensor data generated by one or more remote devices;

training a machine learning model to generate a marker for the measurement goal, the machine learning model being trained based on the sensor data to generate markers based on input that is based on sensor data;

receiving second sensor data from the user device over a communication network;

using the trained machine learning model to generate a marker for the measurement goal, the marker being generated by the trained machine learning model as a result of processing input that is based on the second sensor data; and transmitting the generated marker to the user device over the communication network such that the user device uses the generated marker to perform access control involving a device, an application, a network, a website, or a physical space.

2. The system of claim 1, wherein:
the operations further comprise retrieving a stored marker; and
training the machine learning model is based on the stored marker.

3. The system of claim 1, wherein the marker is configured to generate an estimate of a likelihood that the measurement goal may be satisfied at a future time, the estimate being based on the second sensor data.

4. The system of claim 1, wherein the machine learning model comprises at least one of a neural network model, a recurrent neural network model, a random forest model, or a support vector model.

5. The system of claim 1, wherein training the machine learning model comprises training a fuzzy logic model.

6. The system of claim 1, wherein training the machine learning model is unsupervised.

7. The system of claim 1, the operations further comprising:
determining, based on the second sensor data, that the measurement goal is satisfied or that the marker satisfies a condition; and
executing a triggering action based on at least one of the measurement goal or the marker, the triggering action comprising at least one of:
sending an instruction to the user device to control access to the user device;
sending an instruction to the user device to control access to an application stored on the user device;
sending an instruction to the user device to control access of the user device to a network;
sending an instruction to the user device to control access of the user device to a website; or
sending a command to a remote device, the command comprising an instruction to control access to a physical space.

8. The system of claim 1, wherein the measurement goal includes at least one of an internet use goal, a diet goal, a consumption goal, a sleep goal, an exercise goal, a medical treatment goal, or an activity goal.

9. The system of claim 1, wherein the measurement goal comprises an individual measurement goal that relates to a group measurement goal.

10. The system of claim 1, the operations further comprising:

receiving additional sensor data;
determining, based on the additional sensor data, that at least one of a measurement goal or a marker is satisfied; and
transmitting, based on the determining, an instruction to a remote device to control access to a physical space.

11. The system of claim 1, the operations further comprising:
receiving additional sensor data; and
adjusting the maker marker based on the additional sensor data.

12. The system of claim 1, wherein the user device comprises at least one of a smartphone, a computer, a wearable device, a tablet, a mobile device, a terminal, a kiosk, or a client device.

13. A computer-implemented method comprising:
receiving a measurement goal from a user device, the measurement goal relating to at least one of a behavior or a health status;

obtaining sensor data generated by one or more remote devices;

training a machine learning model to generate a marker for the measurement goal, the machine learning model being trained based on the sensor data to generate markers based on input that is based on sensor data;

receiving second sensor data from the user device over a communication network;

using the trained machine learning model to generate a marker for the measurement goal, the marker being generated by the trained machine learning model as a result of processing input that is based on the second sensor data; and transmitting the generated marker to the user device over the communication network such that the user device uses the generated marker to perform access control involving a device, an application, a network, a website, or a physical space.

14. A non-transitory computer readable medium storing instructions that, when executed by one or more processors, cause the one or more processors to perform operations comprising:
receiving a measurement goal from a user device, the measurement goal relating to at least one of a behavior or a health status;

obtaining sensor data generated by one or more remote devices;

training a machine learning model to generate a marker for the measurement goal, the machine learning model being trained based on the sensor data to generate markers based on input that is based on sensor data;

receiving second sensor data from the user device over a communication network;

using the trained machine learning model to generate a marker for the measurement goal, the marker being generated by the trained machine learning model as a result of processing input that is based on the second sensor data; and transmitting the generated marker to the user device over the communication network such that the user device uses the generated marker to perform access control involving a device, an application, a network, a website, or a physical space.

15. The method of claim 13, further comprising transmitting the trained machine learning model to the user device over the communication network.

16. The method of claim 13, wherein the marker indicates a likelihood that the measurement goal will be satisfied in the future.

17. The method of claim 13, wherein the second sensor data comprises data captured at a time that is partially through a predetermined time period corresponding to the measurement goal, wherein the marker indicates a likelihood that the measurement goal will be satisfied by an end of the predetermined time period.

18. The method of claim 13, wherein the marker includes a function configured to produce an estimated likelihood that the measurement goal will be satisfied in the future.

19. The method of claim 13, wherein the marker includes a threshold.

\* \* \* \* \*